(12) United States Patent
Lafay et al.

(10) Patent No.: US 8,476,455 B2
(45) Date of Patent: Jul. 2, 2013

(54) 1-N-PHENYL-AMINO-1H-IMIDAZOLE DERIVATIVES AND PHARMACEUTICAL COMPOSITIONS CONTAINING THEM

(75) Inventors: Jean Lafay, Nice (FR); Benoit Rondot, Chemin du Caminon (FR); Paule Bonnet, Menton (FR); Thierry Clerc, Vigoulet Auzil (FR); Jacqueline Shields, Nice (FR); Igor Duc, Cannes (FR); Eric Duranti, Saint Laurent du Var (FR); Francois Puccio, Nice (FR); Christian Blot, La Colle sur Loup (FR); Philippe Maillos, Labastide Saint Georges (FR)

(73) Assignee: Laboratoire Theramex, Hereditaire Albert (MC)

( * ) Notice: Subject to any disclaimer, the term of this patent is extended or adjusted under 35 U.S.C. 154(b) by 579 days.

(21) Appl. No.: 10/582,778

(22) PCT Filed: Dec. 15, 2004

(86) PCT No.: PCT/EP2004/014847
§ 371 (c)(1),
(2), (4) Date: Aug. 17, 2006

(87) PCT Pub. No.: WO2005/058842
PCT Pub. Date: Jun. 30, 2005

(65) Prior Publication Data
US 2007/0112009 A1    May 17, 2007

(30) Foreign Application Priority Data

Dec. 15, 2003  (EP) ..................................... 03293152
Nov. 12, 2004  (EP) ..................................... 04292681

(51) Int. Cl.
*C07D 233/44*  (2006.01)
*A61K 31/4164*  (2006.01)

(52) U.S. Cl.
USPC ....................................... 548/326.5; 514/398

(58) Field of Classification Search
USPC ....................................... 548/326.5; 514/398
See application file for complete search history.

(56) References Cited

U.S. PATENT DOCUMENTS

| | | | |
|---|---|---|---|
| 3,558,625 A | 1/1971 | Metuchen et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 4,937,250 A * | 6/1990 | Bowman et al. | 514/341 |
| 4,978,672 A * | 12/1990 | Bowman et al. | 514/383 |
| 5,045,558 A * | 9/1991 | Strehlke et al. | 514/399 |
| 5,071,861 A | 12/1991 | Bowman et al. | |
| 5,674,886 A * | 10/1997 | Okada et al. | 514/383 |
| 6,737,433 B1 * | 5/2004 | Adje et al. | 514/398 |
| 6,762,205 B1 | 7/2004 | Koizumi et al. | |
| 7,098,343 B2 | 8/2006 | Potter et al. | |
| 7,361,677 B2 | 4/2008 | Potter et al. | |
| 2003/0008862 A1 | 1/2003 | Li et al. | |
| 2004/0122024 A1 | 6/2004 | De Clercq et al. | |

FOREIGN PATENT DOCUMENTS

| | | |
|---|---|---|
| DE | 1950491 | 4/1971 |
| DE | 3435173 | 4/1985 |
| WO | 99/52890 A1 | 10/1999 |
| WO | 01/77078 A1 | 10/2001 |
| WO | 02/051821 A1 | 7/2002 |
| WO | 03045925 A1 | 6/2003 |
| WO | 2004/054983 A2 | 7/2004 |
| WO | 2004/101545 A1 | 11/2004 |

OTHER PUBLICATIONS

Wermuth (C. Wermuth, Editor, Practice of Medicinal Chemistry, Academic Press (1996), pp. 203-237).*
Kubinyi (3D QSAR in Drug Design: Ligand-Protein Interactions and Molecular Similarity, vol. 2-3, Springer, 1998, 800 pages). TOC and pp. 243-244 provided.*
Patani et al. (Chem. Rev., 1996, vol. 96, No. 8, p. 3147-3176).*
Supuran et al "Carbonic Anhydrase, It's Inhibitors and Activators", CRC, 2004, title page and table of contents).
Yue et al "Determinants of Tissue Estradiol Levels and Biologic Responsiveness in Breast Tumors" Breast Cancer Research & Treatment 1998 pp. 51-57.
Smith et al "Fadrozole and Letrozole . . . Breast Cancer: Clinical and Biochemical effects" Breast Cancer Research & Treatment 1998 pp. S67-S71.
Singh et al "Biochemical Control of Breast Aromatase" Breast Cancer Research & Treatment 1998 pp. S9-S14.

(Continued)

*Primary Examiner* — Robert Havlin
(74) *Attorney, Agent, or Firm* — Ladas & Parry, LLP

(57) ABSTRACT

The invention relates to the compounds of formula (I):

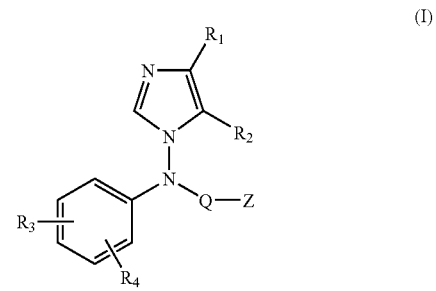

in which $R_1$, $R_2$, $R_3$, $R_4$, Q and Z are as defined in the specification.

The invention also relates to the pharmaceutical compositions containing these compounds.

6 Claims, 1 Drawing Sheet

OTHER PUBLICATIONS

Shenton et al "Comparison of Biochemical Aromatase Activity . . . Imunhistochemistry in Human Breast Carcinomas" Breast Cancer Research & Treatment 1998 pp. S101-S107.

Sasano et al "Immunolocalization of Aromatase in Human Breast Disorders Using Different Antibodies" Breast Cancer Research & Treatment 1998 pp. S79-S84.

Santen et al "Demonstration of Aromatase Activity and Its Regulation in Breast Tumor and Benign Breast Fibroblasts" Breast Cancer Research & Treatment 1998 pp. S93-S99.

Miller et al "Clinical Importance of Intratumoral Aromatase" Breast Cancer Research & Treatment 1998 S27-S32.

Brodie et al "Intratumoral Aromatase Model: The Effects of Letrozole (CGS 20267)" Breast Cancer Research & Treatment 1998 pp. S23-S26.

Lonning et al, "Pharmacological and Clinical Profile of Anastrozole", Breast Cancer Research & Treatment 1998 pp. S53-S57.

Lonning et al, "Pharmacological Profiles of Exemestane and Formestane, Steroidal Aromatase Inhibitors Used for Treatment of Postmenopausal Breast Cancer" Breast Cancer Research & Treatment 1998 pp. S45-S52.

Harada et al "Molecular Analysis of Aberrant Expression of Aromatase in Breast Cancer Tissues" Breast Cancer Research & Treatment 1998 pp. S15-S21.

Goss "Pre-Clinical and Clinical Review of Vorozole, . . . Generation Aromatase Inhibitor" Breast Cancer Research & Treatment 1998 pp. S59-S65.

Dowsett "Theoretical Considerations for the Ideal Aromatase Inhibitor" Breast Cancer Research & Treatment 1998 pp. S39-S44.

"Discussion of Session 1" Breast Cancer Research & Treatment 1998 pp. S33-S37.

"Discussion of Session 2" Breast Cancer Research & Treatment 1998 pp. S73-S77.

"Discussion of Session 3" Breast Cancer Research & Treatment 1998 pp. S109-S119.

Brodie "Aromatase Expression in the Human Breast" Breast Cancer Research & Treatment 1998 pp. S85-S91.

Singh et al "The Regulation of Aromatase Activity in Breast Fibroblasts: The Role of Interleukin-6 and Prostaglandin $E_2$" Endocrine-Related Cancer 1999 pp. 139,147.

Simpson et al "Local Estrogen Biosynthesis in Males and Females" 1999 Endocrine-Related Cancer, pp. 131-137.

Sasano et al "Effects of Aromatase Inhibitors on the Pathobiology of Human Breast, Endometrial and Ovarian Carcinoma" 1999 Endocrine-Related Cancer pp. 197-204.

Santen et al "The Potential of Aromatase Inhibitors in Breast Cancer Prevention" 1999 Endocrine-Related Cancer pp. 235-243.

Santen et al "Use of Aromatase Inhibitors in Breast Carcinoma" 1999 Endocrine-Related Cancer pp. 75-92.

Ragaz "Status of Aromatase Inhibitors in Relation to Other Breast Cancer Treatment Modalities" 1999 Endocrine-Related Cancer pp. 277-291.

Probst-Hensch et al "Aromatase and Breast Cancer Susceptibility" 1999 Endocrine-Related Cancer pp. 165-173.

Osborne "Aromatase Inhibitors in Relation to Other Forms of Endocrine Therapy for Breast Cancer" 1999 Endocrine-Related Cancer pp. 271-276.

Miller "Biology of Aromatase Inhibitors:Pharmacology/Endocrinology Within the Breast" 1999 Endocrine-Related Cancer pp. 187-195.

Manni "Hormonal Approaches to the Chemo-Prevention of Endocrine-Dependent Tumors" 1999. Endocrine-Related Cancer pp. 483-485.

Ingle et al "Combination Hormonal Therapy Involving Aromatase Inhibitors in the Management of Women with Breast Cancer" 1999 Endocrine-Related Cancer pp. 265-269.

Lonning "Cross-resistance to different Aromatase Inhibitors in Breast Cancer Treatment" 1999 Endocrine-Related Cancer pp. 251-257.

Harada et al "Aromatase Inhibitors and Enzyme Stability" 1999 Endocrine-Related Cancer pp. 211-218.

Goss "Risks Versus Benefits in the Clinical Application of Aromatase Inhibitors" 1999 Endocrine-Related Cancer pp. 325-332.

Feuillan et al "Use of Aromatase Inhibitors in Precocious Puberty" 1999 Endocrine-Related Cancer pp. 303-306.

Dowsett "Drug and Hormone Interactions of Aromatase Inhibitors" 1999 Endocrine-Related Cancer pp. 181-185.

Dixon et al "Lessons From the Use of Aromatase Inhibitors in the Neoadjuvant Setting" 1999 Endocrine-Related Cancer pp. 227-230.

Coombes et al "Aromatase Inhibitors and Their Use in the Sequential Setting" 1999 Endocrine-Related Cancer pp. 259-263.

Chen et al "Breast tumor Aromatase:Functional Role and Transcriptional Regulation" 1999 Endocrine-Related Cancer pp. 149-156.

Buzdar "Role of Aromatase Inhibitors in Advanced Breast Cancer" 1999 Endocrine-Related Cancer pp. 219-225.

Bulun et al "Estrogen Production in Endometriosis and Use of Aromatase Inhibitors to Treat Endometriosis" Endocrine-Related Cancer pp. 293-301.

Brodie et al "Aromatase and its Inhibitors:New Biology and Clinical Perspectives" 1999 Endocrine-Related Cancer pp. 127-130.

Brodie et al "Aromatase Inhibitors and their Antitumor Effects in Model Systems" 1999 Endocrine-Related Cancer pp. 205-210.

Braunstein "Aromatase and Gynecomastia" 1999 Endocrine-Related Cancer pp. 315-324.

Baum "Use of Aromatase Inhibitors in the Adjuvant Treatment of Breast Cancer" 1999 Endocrine-Related Cancer pp. 231-234.

Smith "Aromatase Inhibitors:a Dose-Response Effect?" 1999 Endocrine-Related Cancer pp. 245-246.

Tekmal et al "Aromatase Overexpression and Breast Hyperplasia, . . . and Aromatase Inhibitors Abrogate these Preneoplastic Changes in Mammary Glands" 1999 Endocrine-Related Cancer pp. 307-314.

Yue et al "Aromatase Within the Breast" 1999 Endocrine-Related Cancer pp. 157-164.

Adams et al "Pyrimidinylimidazole Inhibitors of CSBP/P38 Kinase Demonstrating Decreased Inhibition of Hepatic Cytochrome P450 Enzymes" Bioorganic & Medicinal Chemistry Letters 8, 1998, pp. 3111-3116.

Ahmed et al "Evidence for the Mechanism of the Irreversible Inhibition of Oestrone Sulphatase (ES) by Aminolsulphonate Based Compounds" Journal of Steroid Biochemistry & Molecular Biology 80, 2002, pp. 429-440.

Ahmed et al "Review of Estrone Sulfatase and its Inhibitors—An Important New Target Against Hormone Dependent Breast Cancer" Current Medicinal Chemistry 2002, pp. 262-273.

Andersen et al "1,2,3-Benzoxathiazole 2,2-Dioxides: Synthesis, Mechanism of Hydrolysis, and Reactions with Nucleophiles" J. Org. Chem 1991, pp. 6508-6516.

Becker et al "Notiz zur Kupplung von 4-Hydroxy-pyridazinen" Journal fur Praktisehe Chemie1970, pp. 591-602.

Boger et al "Diels-Alder Reactions of Heterocyclic Azadienes: Total Synthesis of PDE I, PDE II, and PDE I Dimer Methyl Ester" J. Am. Chem Soc. 1987, pp. 2717-2727.

Bonjouklian "A Direct Synthesis of Benzothiophene-3-Carboxylic Acid From Benzothiophene" Synthetic Communications15(8), 1985, pp. 711-713.

Bordwell et al "The Reduction of Sulfones to Sulfides" JACS 1951, pp. 2251-2253.

Bordwell et al "Studies in the Thianaphthene Series.[1] II Aminothianaphthene-1-dioxides[2]" JACS 1951, pp. 1955-1958.

Bredereck et al "Synthesen und Reaktionen von 4-Chlor-5-cyanpyrimidin. Synthese von 4-Amino- und 4-Hydroxy-pyrimidinaldehyd-(5)" Chem. Ber 100, 1967, pp. 3664-3670.

Budesinsky et al "Long-Acting Sulphonamides. IV, Reductive Cleavage of the Ether Bond in the Pyrimidine and Pyridine Series" Czech. Chem. Community 1968, pp. 2266-2275.

Burawoy et al "Electronic Spectra of Organic Molecules and their Interpretatio Part I." J. Chemical Society 1955, pp. 2557-2563.

Cannizzo et al "Synthesis of Substituted [1] Benzothienol[2,2-b]pyrazines" J. Heterocyclic Chem., 1990, pp. 2175-2179.

Castiglione-Gertsch "New Aromatase Inhibitors: More Selectivity, Less Toxicity, Unfortunately, the Same Activity" EP J. of Cancer, 1996, pp. 393-395.

Chapman et al "Thieno[2,2-b][1]Benzothiophen and Thieno [3,2-b][1]Benzothiophen. Part 1. Preparation" J. Chem. Soc. 1970, pp. 2431-2435.

Chung et al "Friedel-Crafts Cyclization of 2-(3-Indolythio)propionic Acids. An Unusual Rearrangement Leading to 4-Sulfur-Substituted Tricyclic Indoles" Tetrahedron Letters, 1992, pp. 4717-4720.

Cooper et al "A Concise Synthesis of Either Enantiomer of Azatyrosine" Bioorganic & Medicinal Chemistry Letters, 1996, pp. 2613-2616.

Daves et al "Pyrimidines. II. Orotic Acid Analogs" Midwest Research Institute 1960, pp. 2755-2763.

Daynes et al "Regulation of Murine Lymphokine Production in Vivo" J. Exp. Med. 1990, pp. 979-996.

Dibbelt et al "Human Placental Sterylsulfatase" Biol. Chem. Hoppe-Seyler, 1991, pp. 173-185.

Drabowicz et al "Deoxygenation of Sulfoxides, A Review" Organic Preparation and Procedures Int. 1977, pp. 63-83.

Ellefson et al "Synthesis and Evaluation of 1,2,3,4-Tetrahydro[1]benzothieno[2m2-h]isoquinolines as Dopamine Antagonists" J. Med. Chem. 1981, pp. 1107-1110.

Felder et al "97. Uber die Herstellung von 2-Amino-5-5Pyrazincarbonsaure und Derivaten" vol. 47, Helv. Chim. Acta., 1964, pp. 873-876.

Felix et al "Rapid Removal of Protecting Groups from Peptides by Catalytic Transfer Hydrogenation with 1,3-Cyclohexadiene" J. Org. Chem. 1978, pp. 4194-4196.

Fischer "Can N-Alkyl- and N-Arylimidazoles be Prepared Directly from Alcohols and Phenols with N,N'-Carbonyldiimidazole?" Ciba Specialty Chemicals, 2002, pp. 29-30.

Golob et al "Sulfamoyloxy-Substituted 2-Phenylindoles: Antiestrogen-Based Inhibitors of the Steroid Sulfatase in Human Breast Cancer Cells" Bioorganic & Medicinal Chemistry 10, 2002, pp. 3941-3953.

Graham et al "Topically Active Carbonic Anhydrase Inhibitors. 2. Benzo[b]thiophenesulfonamide Derivatives with Ocular Hypotensive Activity" J. Med. Chem. 1989, pp. 2548-2554.

Huffman et al "Reaction of s-Triazine with Acidic α-Methylene Compounds" J. Org. Chem. 1962, pp. 551-558.

Isoda et al "Medicinal Chemical Studies on Antiplasmin Drugs. VI[1] Aza Analogs of 4-Aminomethylbenzoic Acid" Chem. Pharm. Bull. 1980, pp. 1408-1414.

Ivanov et al "Down-regulation of Transmembrane Carbonic Anhydrases in Renal Cell Carcinoma Cell Lines by Wild-type von Hippel-Lindau Transgenes" Proc. Natl. Acad. Medical Sciences, 1998, pp. 12596-12601.

Johnson et al "The Effect of Steroid Sulfatase Inhibition on Learning and Spatial Memory", Brain Research, 2000, pp. 286-290.

Jonat et al "A Randomised Trial Comparing Two Doses of the New Selective Aromatase Inhibitor Anastrozole (Arimidex) with Megestrol Aceetate in Postmenopausal Patients with Advanced Breast Cancer" EP Journal of Cancer, 1996, pp. 404-412.

Koguro et al "Novel Synthesis of 5-Substituted Tetrazoles from Nitriles" Synthesis, 1998, pp. 910-914.

Kunieda et al "Preparation and Photochemistry of Pyrimidine Nucleoside Sulfonium Ylides" J. Am. Chem. Soc., 1971, pp. 3487-3493.

Lerch et al "Selective Alkylation of Phenylhydrazine: A Facile and Efficient Synthesis of 1-Alkyl-1-phenylhydrizines" Synthesis, 1983, pp. 157-158.

Lutz et al "Isomerism in the Direct Chlorination of 2-Methylpyrazine" J. Org. Chem., 1964, pp. 415-418.

MacCarthy-Morrough et al "Differential Effects of Estrone and Estsrone-3-0-Sulfamate Derivatives on Mitotic Arrest, Apoptosis, and Microtubule Assembly in Human Breast Cancer Cells" Cancer Research 60, 2000, pp. 5441-5450.

Mann et al "Keratinocyte-Derived Granulocyte-Macrophage Colony Stimulating Factor Accelerates Wound Healing: Stimulation of Keratinocyte Proliferation, Granulation Tissue Formation, and Vascularization" J. Invest. Derm., 2001, pp. 1382-1390.

MARCH Advanced Organic Chemistry Reactions, 4th ed., Wiley Interscience, NY. pp. 1792-1805.

MARCH Advanced Organic Chemistry Reactions, 4th ed., Wiley Interscience, NY. pp. 1295-1296.

MARCH Advanced Organic Chemistry Reactions, 4th ed., Wiley Interscience, NY pp. 555-559.

Matassa et al "Synthesis and in Vitro LTD$_4$ Antagonist Activity of Bicyclic and Monocyclic Cyclopentylurethane and Cyclopentylacetamide N-Arylsulfonyl Amides" M. Med. Chem., 1990, pp. 2621-2629.

Matecka et al "Heteroaromatic Analogs of 1-[2-(Diphenylmethoxy)ethyl]- and 1-[2-[Bis(4-Fluorophenyl)methoxy]ethyl]-3-(3-phenylpropyl)piperazines (GBR 12935 and GBR 12909) as High-Affinity Dopamine Reuptake Inhibitors" J. Med. Chem 1997, pp. 705-716.

McOmie et al "Demethylation of Aryl Methyl Ethers by Boron Tribromide" Tetrahedron, 1968, pp. 2289-2292.

Meerpoel et al "Synthesis of 6-Methoxy- and 6-Chloro-2(1H)-Pyridinone Acyclo-C-Nucleosides from 2H-1,4-Oxazin-2-ones" Tetrahedron, 1993, pp. 4085-4098.

Myers et al "A Practical Synthesis of L-Azatyrosline" J. Org. Chem. 1996, pp. 813-815.

Nishioka et al "Regioselective Dealkylation of 2-Alkoxybenzoic Acid and its Amide Derivatives with Aliphatic Amines" Synthesis 2000, pp. 243-246.

Okada et al "Efficient General Method for Sulfamoylation of a Hydroxyl Group" Tetrahedron Letters 414, 2000, pp. 7047-7051.

Ong et al "[(6,7-Dichlorobenzo[b]thien-5-yl)oxy]acetic Acids and 1,1-Dioxides.[1] I. A Structurally Novel Class of Diuretics with Hypotensive Activity" J. Med. Chem. 1987, pp. 2295-2303.

Nussbaumer et al "2-Substituted 4-(Thio)chromenone 6-O-Sulfamates: Potent Inhibitors of Human Steroid Sulfatase" J. Med. Chem. 2002, pp. 4310-4320.

Parkkila et al "Immunohistochemical Demonstration of Human Carbonic Anhydrase Isoenzyme II in Brain Tumours" Histochemical Journal 27, 1995, pp. 974-982.

Parkkila et al "Carbonic Anhydrase Inhibitor Suppresses Invasion of Renal Cancer Cells in vitro" Proc. Natl. Acad. Sci., USA,2000, pp. 2220-2224.

Nussbaumer et al "Steroid Sulfatase Inhibitors" Medicinal Research, 2004, pp. 529-576.

Parkkila et al "Immunohistochemical Demonstration of the Carbonic Anhydrase Isoenzymes I and-II in Pancreatic Tumours" Histochemical Journal 27, 1995, pp. 133-138.

Pasqualini et al "Estrone Sulfatase Versus Estrone Sulfotransferse in Human Breast Cancer: Potential Clinical Applications" Journal of Steroid Biochemistry etc., 1999, pp. 287-292.

Piras et al "Synthesis and Evaluation of Gastroprotective Activity of Omeprazole Related Benzimidazole, Imidazo[4,50b] Ppyridine and Quinoxaline 20Substituted Derivatives", Il Farmaco 1993, pp. 1249-1259.

Woo et al "First Dual Aromatase-Steroid Sulfatase Inhibitors" J. Med. Chem. 2003, pp. 3193-3196.

Purohit et al "In Vivo Inhibition of Estrone Sulfatase Activity and Growth of Nitrosomethylurea-induced Mammary Tumors by 667 Coumate[1]" Cancer Research 60, 2000, pp. 3394-3396.

Purohit et al "Non-steroidal and Steroidal Sulfamates: New Drugs for Cancer Therapy" Molecular and Cellular Endocrinology 171, 2001, pp. 129-135.

Reed et al "Sulphatase Inhibitors: the Rationale for the Development of a New Endocrine Therapy" Reviews on Endocrine-Related Cancer 1993, pp. 51-62.

Grivas et al "Facile Desulfurization of Cyclic Thioureas by Hydrogen Peroxide in Acetic Acid" Acta Chemica Scandinavica 49, 1996, pp. 225-229.

Sall et al "Diamino Benzo [b] thiophene Derivatives as a Novel Class of Active Site Directed Thrombin Inhibitors, 5, Potency, Efficacy, and Pharmacokinetic Properties of Modified C-3 Side Chain Derivatives" J. Med Chem. 2000, pp. 649-663.

Sato et al "Studies on Pyrazines, 7(1), The Eynthesis of 5-Chloropyrazinecarboxylic Acid" J. Heterocyclic Chem., 1982, pp. 407-408.

Schreiner et al "Estrone Formate: a Novel Type of Irreversible Inhibitor of Human Steroid Sulfatase" Bioorganic & Medicinal Chemistry Letters 14, 2004, pp. 4999-5002.

Simpson et al "Aromatase Expression in Health and Disease" Endocrine Society, 1997, pp. 185-214.

Simpson et al "ARomatase Cytochrome P450, the Enzyme Responsible for Estrogen Biosynthesis" Endoctrine Society 1994, pp. 342-355.

Stein et al "Cloning and Expression of Human Steroid-sulfatase" The Journal of Biological Chemistry 1989, pp. 13865-13872.

Suitters et al "Immune Enhancing Effects of Dehydroepiandrosterone and Dehydroepiandrosterone Sulphate and the Role of Steroid Sulphatase" Immunology 1997, pp. 314-321.

Svoboda et al "Synthesis and Biological Evaluation of New Antiinflammatory 1-Benzothiophene-2-Carboxanilides" Czech. Cham. Commun (vol. 65) 2000, pp. 1082-1092.

Lapierre et al "The Difluoromethylene Group as a Replacement for the Labile Oxygen in Steroid Sulfates: a New Approach to Steroid Sulfatase Inhibitors" Bioorganic & Medicinal Chemistry Letters 14, 2004, pp. 151-155.

Tilley et al "Biphenylearboxamide Derivatives as Antagonists of Platelet-Activating Factor" J. Med. Chem 1989, pp. 1814-1820.

Turnbull et al "Activated Carbonyl Species for the Preparation of ortho-Acylarylsydnones" J. Heterocyclic Chem., 2000, pp. 383-388.

Winum et al "Carbonic Anhydrase Inhibitors. Inhibition of Cytosolic Isozymes I and II and Transmembrane, Tumor-Associated Isozyme IX with Sulfamates Including EMATE Also acting as Steroid Sulfatase Inhibitors" J. Med. Chem. 2003 pp. 2197-2204.

Wolf et al "Actions of Dehydroepiandrosterone and its Sulfate in the Central Nervous System: Effects on Cognition and Emotion in Animals and Humans" Brain Research Rev., 1999, pp. 264-288.

Yanai et al "A New Alkylation of Pyridazines with Nitromethane and Nitroethane" Heterocycles, vol. 4, No. 8, 1976, pp. 1331-1335.

* cited by examiner

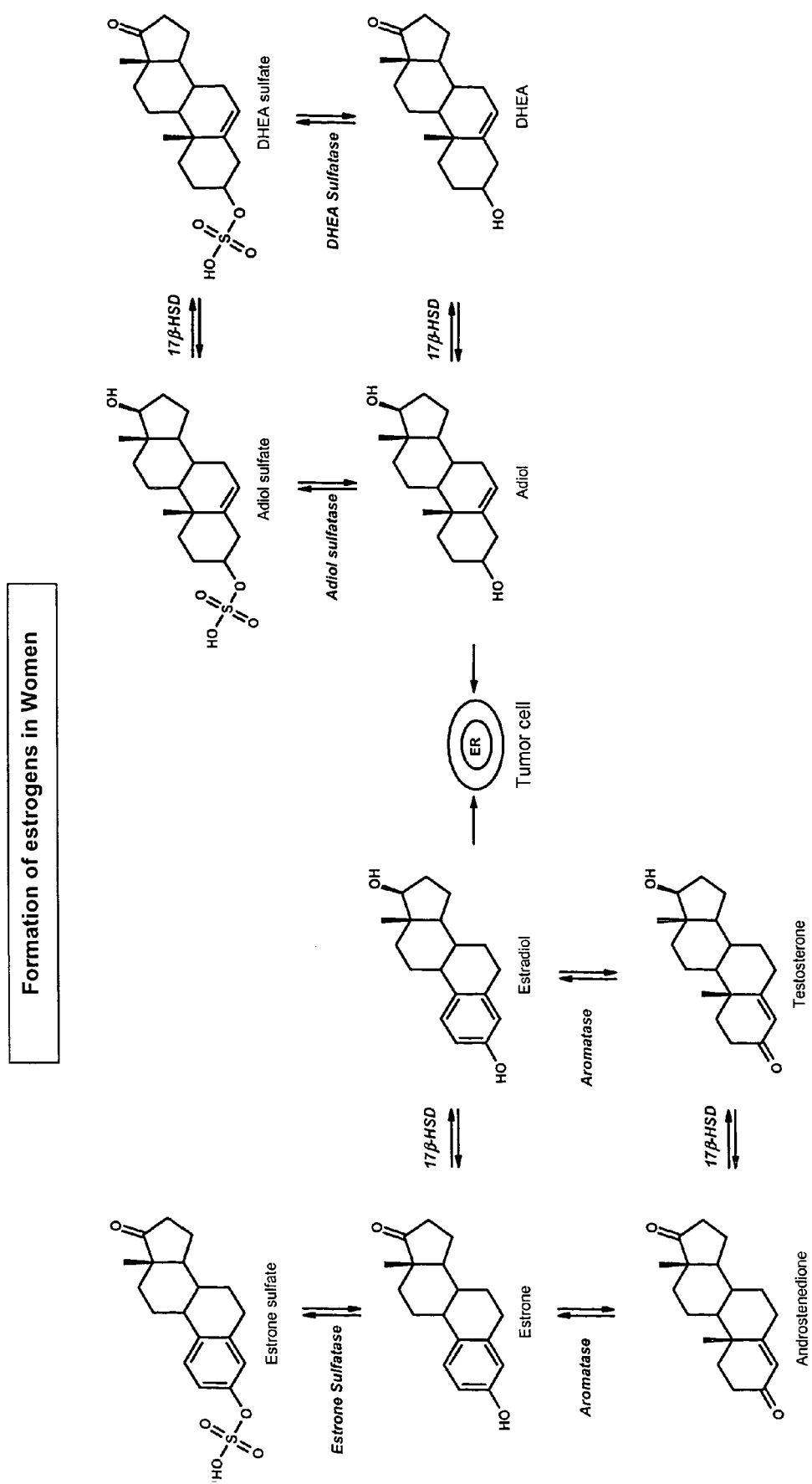

1-N-PHENYL-AMINO-1H-IMIDAZOLE DERIVATIVES AND PHARMACEUTICAL COMPOSITIONS CONTAINING THEM

This application is a filing under 35 USC 371 of PCT/EP2004/014847, filed Dec. 15, 2004.

BACKGROUND OF THE INVENTION

The present invention relates to 1-N-phenylamino-1H-imidazole derivatives and to pharmaceutical compositions containing them.

The invention generally relates to the field of hormone- and non hormone-dependent cancer and endocrine disorders.

Aromatase is the physiological enzyme responsible for the specific conversion of androgens such as androstenedione or testosterone, into estrogens such as estrone and estradiol, respectively (Simpson E R et al., Endocrine Reviews, 1994, 15: 342-355). Inhibition of aromatase is, therefore, a strategy of choice to interfere with normal or pathological estrogen-induced or estrogen-dependent biological processes such as female sexual differentiation, ovulation, implantation, pregnancy, breast and endometrial cell proliferation as well as regulations of spermatogenesis or prostate cell proliferation in male or of non-reproductive functions such as bone formation or immune T cell and cytokine balance (see Simpson E R et al., Recent Progress in Hormone Research, 1997, 52: 185-213 and the whole issues of Endocrine Related Cancer (1999, volume 6, no 2) and Breast Cancer Research Treatment (1998, volume 49, supplement no 1)).

The enzyme steroid sulfatase (E.C. 3.1.6.2, STS) catalyses the hydrolysis of estrone sulfate to estrone and the DHEA sulfate to DHEA (Dibbelt L, Biol. Chem, Hoppe-Seyler, 1991, 372, 173-185 and Stein C, J. Biol. Chem., 1989, 264, 13865-13872).

The steroid sulfatase pathway has been the focus of recent interest in the context of breast cancer, with regard to the local intra-tissue formation of estrogens from the abundant circulating pool of estrone sulfate ($E_1S$) (Pasqualini J R, J. Steroid Biochem. Mol. Biol., 1999, 69, 287-292 and Purohit A, Mol. Cell. Endocrinol., 2001, 171, 129-135).

Inhibition of this enzyme would prevent EIS from yielding free estrone ($E_1$), which can be transformed into estradiol ($E_2$) by enzymatic reduction. In addition to the estrone sulfatase pathway, it is now believed that another potent estrogen, androstenediol (adiol) obtained from DHEA after hydrolysis of DHEA-S, could be another important contributor, in the support of growth and development of hormone-dependent breast tumors.

The formation of estrogens in women is schematically represented in FIG. 1.

In patients with hormone-dependent cancers, aromatase inhibitors are currently used to prevent estrogen synthesis. However, clinical trials showed a relative lack of efficacy for patients with estrogen receptor-positive tumors (Castiglione-Gertsch M, Eur. 3. Cancer, 1996, 32A, 393-395 and Jonat W, Eur. J. Cancer, 1996, 32A, 404-412). As an explanation, steroid sulfatase pathway could be another important route for estrogen formation in breast tumors.

EMATE (Ahmed S, Curr. Med. Chem., 2002, 9, 2, 263-273), estrone-3-sulfamate, is the historical standard steroidal sulfatase inhibitor but has the major drawback of being estrogenic because of its mechanism of inhibition: the sulfamate moiety is cleaved during the process of enzyme inactivation, which releases $E_1$, not from EIS but from EMATE itself (Ahmed S, J. Steroid Biochem. Mol. Biol., 2002, 80, 429-440).

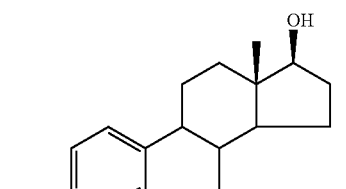

Estradiol

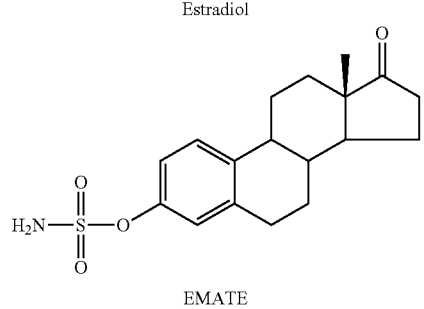

EMATE

Other non-steroid sulfamate compounds which release derivatives without estrogenic properties have been presented as acceptable drug candidates such as 6,6,7-COUMATE, a standard non-estrogenic sulfatase inhibitor from the literature (Purohit A, Cancer Res, 2000, 60, 3394-3396).

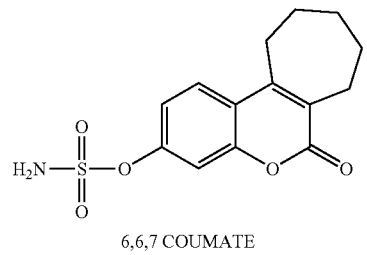 [SMILES: NS(=O)(=O)Oc1ccc2c3c(c(=O)oc2c1)CCCCC3]

6,6,7 COUMATE

Human carbonic anhydrases catalyse the conversion between carbon dioxide ($CO_2$) and the bicarbonate ion ($HCO_3^-$), and are involved in physiological and pathological processes. They include hormone-dependent and non-hormone-dependent cancerogenesis, metastasis invasive process and hypoxic tumors that express these enzymes which are less responsive to classical chemo/radio-therapy inhibitors. In particular, EMATE was found to have a human carbonic anhydrase inhibitory potency similar to that of acetazolamide, a well-known sulfonamide human carbonic anhydrase inhibitor (Winum 3 and al., J. Med. Chem. 2003, 46, 2197-2204).

It is therefore of particular interest to have compounds with at least one, preferably at least two of the following activities: aromatase inhibition, steroid sulfatase inhibition and carbonic anhydrase inhibition.

Recently, B. Potter et al. (J. Med. Chem., 46, 2003, 3193-3196) reported that sulfamoylated-derivatives of the aromatase inhibitor YM 511 inhibited sulfatase and aromatase activity in JEG-3 cells.

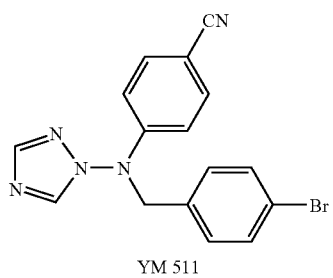 [SMILES: N#Cc1ccc(N(Cc2ccc(Br)cc2)n2cncn2)cc1]

YM 511

Compounds presented as useful for the treatment of estrogen-dependent diseases, are described in U.S. 2003/0008862A. Imidazole derivatives with anti-aromatase properties are described in WO 2004/054983.

SUMMARY OF THE INVENTION

It has now been found that imidazole derivatives which contain a 1-N-phenylamino group, demonstrate an unexpectedly high potency to inhibit aromatase and/or steroid sulfatase and/or carbonic anhydrase.

Accordingly, one object of this invention is to provide 1-N-phenylamino-1H-imidazole derivatives, which are potent aromatase and/or steroid sulfatase and/or carbonic anhydrase inhibitors.

Another object of this invention is to provide a pharmaceutical composition containing, as active ingredient, a 1-N-arylamino-1H-imidazole derivative as depicted below.

A further object of this invention is to provide the use of 1-N-phenylamino-1H-imidazole derivatives in the manufacture of a medicament for treating or preventing various diseases and for managing reproductive functions in women, in men as well as in female and male wild or domestic animals.

DETAILED DESCRIPTION OF THE INVENTION

The 1-N-phenylamino-1H-imidazole derivatives of this invention are represented by the following general formula (I):

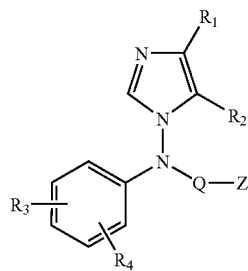

(I)

and add addition salts and stereoisomeric forms thereof, wherein:

$R_1$ and $R_2$ are each independently hydrogen, a ($C_1$-$C_6$)alkyl or a ($C_3$-$C_8$)cycloalkyl; or $R_1$ and $R_2$ together form a saturated or unsaturated 5-, 6- or 7-membered carbocyclic ring;

Q is $(CH_2)_m$—X—$(CH_2)_n$-A;

A is a direct link, O, S, SO, $SO_2$, $NR_5$;

X is a direct link, $CF_2$, O, S, SO, $SO_2$, C(O), $NR_5$ or $CR_6R_7$;

Z is a group selected from:

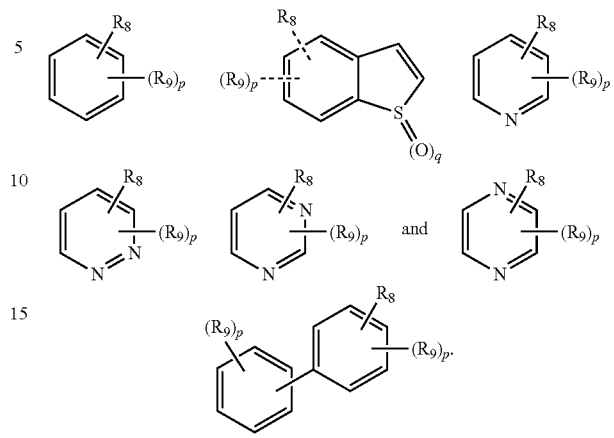

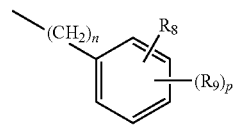

m and n are each independently 0, 1, 2, 3 or 4;
p is 1, 2, 3 or 4;
q is 0, 1 or 2;
the dotted line means that $R_8$ and/or $R_9$ can be on any position of the benzothiophene ring;

$R_3$ and $R_8$ are each independently hydrogen or a hydroxy, cyano, halogen, nitro, ($C_1$-$C_6$)alkyl, ($C_1$-$C_6$)alkoxy, trifluoromethyl, ($C_1$-$C_6$)alkylthio, ($C_1$-$C_6$)alkylsulfonyl, acyl, ($C_1$-$C_6$)alkoxycarbonyl, carboxamido, OPO$(OR_{10})_2$, $NR_{10}R_{11}$, $SO_2NR_{10}R_{11}$, $OSO_2NR_{10}R_{11}$, $OSO_2OR_{10}$, $SO_2OR_{10}$, $SSO_2NR_{10}R_{11}$, $CF_2SO_2OR_{10}$, $CF_2SO_2NR_{10}R_{11}$, $CF_2$-tetrazolyl or $NR_{12}SO_2NR_{10}R_{11}$, $OSO_2NR_{12}SO_2NR_{10}R_{11}$, $CO_2R_{10}$, $CONR_{10}R_{11}$, OCHO, $OCONR_{10}R_{11}$, $OCSNR_{10}R_{11}$, $SCONR_{10}R_{11}$, $SCSNR_{10}R_{11}$, tetrazolyl, $NR_{12}CONR_{10}R_{11}$, $NR_{10}$—CHO group;

when Q-Z is

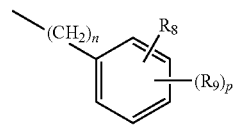

n is 0, 1 or 2 and p is 1, one of $R_3$ and $R_8$ is a hydroxy, nitro, $OPO(OR_{10})_2$, $NR_{10}R_{11}$, $OSO_2NR_{10}R_{11}$, $OSO_2OR_{10}$, $SO_2OR_{10}$, $SSO_2NR_{10}R_{11}$, $CF_2SO_2OR_{10}$, $CF_2SO_2NR_{10}R_{11}$, $CF_2$-tetrazolyl, $NR_{12}SO_2NR_{10}R_{11}$ $OSO_2NR_{10}SO_2NR_{11}R_{12}$, $CO_2R_{10}$, $CONR_{10}R_{11}$, OCHO, $OCONR_{10}R_{11}$, $OCSNR_{10}R_{11}$, $SCONR_{10}R_{11}$, $SCSNR_{10}R_{11}$, tetrazolyl, $NR_{12}CONR_{10}R_{11}$, $NR_{10}$—CHO group and the other is hydrogen or a hydroxy, cyano, halogen, nitro, ($C_1$-$C_6$)alkyl, ($C_{1-6}$)alkoxy, trifluoromethyl, ($C_1$-$C_6$)alkylthio, ($C_1$-$C_6$)alkylsulfonyl, acyl, ($C_1$-$C_6$)alkoxycarbonyl, carboxamido, $NR_{10}R_{11}$, $SO_2NR_{10}R_{11}$, $OSO_2NR_{10}R_{11}$, $OSO_2OR_{10}$, $SO_2OR_{10}$, $SSO_2NR_{10}R_{11}$, $CF_2SO_2OR_{11}$, $CF_2SO_2NR_{10}R_{11}$, $CF_2$-tetrazolyl, $NR_{12}SO_2NR_{10}R_{11}$, $OSO_2NR_{12}SO_2NR_{10}R_{11}$, $CO_2R_{10}$, $CONR_{10}R_{11}$, OCHO, $OCONR_{10}R_{11}$, $OCSNR_{10}R_{11}$, $SCONR_{10}R_{11}$, $SCSNR_{10}R_{11}$ tetrazolyl, $NR_{12}CONR_{10}R_{11}$, $NR_{10}$—CHO group;

$R_4$ and $R_9$ are each independently hydrogen or a hydroxy, cyano, halogen, nitro, $OPO(OR_{10})_2$, ($C_1$-$C_6$)alkyl, ($C_1$-$C_6$)alkoxy, trifluoromethyl, ($C_1$-$C_6$)alkylthio, ($C_1$-$C_6$)alkylsulfonyl, acyl, ($C_1$-$C_6$)alkoxycarbonyl, carboxamido, $NR_{10}R_{11}$, $SO_2NR_{10}R_{11}$, $OSO_2NR_{10}R_{11}$, $OSO_2OR_{10}$ $SO_2OR_{10}$, $SSO_2NR_{10}R_{11}$, $CF_2SO_2OR_{10}$, $CF_2SO_2NR_{10}R_{11}$, $CF_2$-tetrazolyl, $NR_{12}SO_2NR_{10}R_{11}$, $OSO_2NR_{12}SO_2NR_{10}R_{11}$, $C_2R_{10}$, CHO, $CONR_{10}R_{11}$, OCHO, $OCONR_{10}R_{11}$, $OCSNR_{10}R_{11}$, $SCONR_{10}R_{11}$, $SCSNR_{10}R_{11}$, tetrazolyl, $NR_{12}CONR_{10}R_{11}$, $NR_{10}$—CHO group;

when p is 2, 3 or 4 the $R_9$s can be the same or different;

$R_6$ and $R_7$ are independently hydrogen, halogen, a $(C_1-C_6)$ alkyl or a $(C_3-C_8)$cycloalkyl;

$R_5$, $R_{10}$, $R_{11}$ and $R_{12}$ are each independently hydrogen, hydroxy, a $(C_1-C_6)$alkyl, or a $(C_3-C_8)$cycloalkyl; $R_{10}$ can also be a salt; $R_{10}$ and $R_{11}$ can also form, together with the nitrogen atom to which they are bound, a 5- to 7-membered heterocycle containing one or two heteroatoms selected from O, S and N;

when Z is

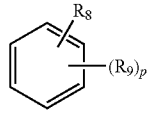

and p is 1, then $R_8$ and $R_9$ can also form together with the phenyl ring a benzoxathiazine dioxide, a dihydrobenzoxathiazine dioxide, a benzoxathiazinone dioxide, a benzoxathiazole dioxide, a benzoxadithiadiazine tetraoxide, a benzodithiazine tetraoxide or a benzodioxadithline tetraoxide;

when Z is

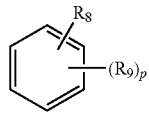

$R_3$ and $R_4$ together with the phenyl ring bearing them can also form a benzofurane or a N-methylbenzotriazole, provided that when p is 1 and Q is $(CH_2)_n$, then, $R_8$ and $R_9$ are independently a hydroxy, nitro, $OPO(OR_{10})_2$, $NR_{10}R_{11}$, $OSO_2NR_{10}R_{11}$, $OSO_2OR_{10}$, $SO_2OR_{10}$, $SSO_2NR_{10}R_{11}$, $CF_2S_2OR_{10}$, $CF_2SO_2NR_{10}R_{11}$, $CF_2$-tetrazolyl, $NR_{12}SO_2NR_{10}R_{11}$, $OSO_2NR_{12}SO_2NR_{10}R_{11}$, $CO_2R_{10}$, $CONR_{10}R_{11}$, OCHO, $OCONR_{10}R_{11}$, $OCSNR_{10}R_{11}$, $SCONR_{10}R_{11}$, $SCSNR_{10}R_{11}$, tetrazolyl, $NR_{12}CONR_{10}R_{11}$, or $NR_{10}$—CHO group.

The present invention also concerns the addition salts of the invention compounds or the stereoisomeric forms thereof, when they exist.

In the description and claims, the term "$(C_1-C_6)$alkyl" is understood as meaning a linear or branched hydrocarbon chain having 1 to 6 carbon atoms. A $(C_1-C_6)$alkyl radical is for example a methyl, ethyl, propyl, isopropyl, butyl, isobutyl, tert-butyl, pentyl, isopentyl or hexyl radical. Preferred alkyl radicals are those having 1, 2 or 3 carbon atoms.

The term "halogen" is understood as meaning a chlorine, bromine, iodine or fluorine atom.

The term "$(C_3-C_6)$cycloalkyl" is understood as meaning a saturated monocyclic hydrocarbon having 3 to 8 carbon atoms. A $(C_3-Q)$cycloalkyl radical is for example a cyclopropyl, cyclobutyl, cyclopentyl, cyclohexyl, cycloheptyl or cyclooctyl radical.

The term "$(C_1-C_6)$alkoxy" is understood as meaning a group OR in which R is a $(C_1-C_6)$alkyl as defined above. A $(C_1-C_6)$alkoxy radical is for example a methoxy, ethoxy, propoxy, isopropoxy, butoxy, isobutoxy, tert-butoxy, n-pentyloxy or isopentyloxy radical. Preferred alkoxy radicals are those having 1, 2 or 3 carbon atoms.

The term "acyl" is understood as meaning a group

in which R' is hydrogen or a $(C_1-C_4)$alkyl wherein the term "alkyl" is as defined above. An acyl radical is for example a formyl, an acetyl, a propionyl, a butyryl or a valeryl radical. Preferred acyl radicals are formyl and acetyl.

In the definition of $R_{10}$, a "salt" is understood as meaning an alkali metal salt or alkaline earth metal salt, such as a sodium, potassium, magnesium or calcium salt, or a salt with an ammonium or with an organic amine such as triethylamine, ethanolamine or tris-(2-hydroxyethyl)amine. In the context of the invention, this applies to groups having an $OR_{10}$ moiety.

The 5- to 7-membered heterocycle can be saturated or unsaturated, and includes for example tetrazole, triazole, pyrazole, pyrazolidine, imidazole, imidazolidine, piperidine, piperazine, morpholine, pyrrolidine.

Compounds of formula (I) form add addition salts, for example with inorganic adds such as hydrochloric add, hydrobromic add, sulfuric acid, nitric acid, phosphoric acid and the like or with organic carboxylic acids such as acetic add, propionic acid, glycolic acid, pyruvic acid, oxalic acid, malic acid, fumaric acid, tartaric acid, citric acid, benzoic acid, cinnamic add, mandelic acid, methanesulfonic acid and the like. Especially preferred are those salts which are pharmaceutically acceptable.

Among the compounds of formula (I), those which fulfil at least one of the following conditions are preferred:

$R_3$ and $R_8$ are each independently hydrogen or a hydroxy, cyano, halogen, nitro, $(C_1-C_6)$alkyl, $(C_1-C_6)$alkoxy, trifluoromethyl, $(C_1-C_6)$alkylthio, $(C_1-C_6)$alkylsulfonyl, acyl, $(C_1-C_6)$alkoxycarbonyl, carboxamido, $NR_{10}R_{11}$, $SO_2NR_{10}R_{11}$, $OSO_2NR_{10}R_{11}$, $OSO_2NR_{12}SO_2NR_{10}R_{11}$, OCHO, $NR_{12}SO_2NR_{10}R_{11}$ group;

$R_4$ and $R_9$ are each independently hydrogen or a hydroxy, cyano, halogen, nitro, $(C_1-C_6)$alkyl, $(C_1-C_6)$alkoxy, trifluoromethyl, $(C_1-C_6)$alkylthio, $(C_1-C_6)$alkylsulfonyl, acyl, $(C_1-C_6)$alkoxycarbonyl, carboxamido, $NR_{10}R_{11}$, $OSO_2NR_{10}R_{11}$, $CO_2R_{10}$, CHO, $NR_{12}SO_2NR_{10}R_{11}$ group;

$R_1$ and $R_2$ are each independently hydrogen or $(C_1-C_6)$ alkyl;

$R_{10}$, $R_{11}$ and $R_{12}$ are each independently hydrogen or $(C_1-C_6)$alkyl.

Particularly preferred compounds of a formula (I) are those in which:

one of $R_3$ and $R_8$ is a hydroxy, nitro, $NR_{10}R_{11}$, $OSO_2NR_{10}R_{11}$ or $NR_{12}SO_2NR_{10}R_{11}$ group; and the other is hydrogen or a hydroxy, cyano, halogen, nitro, $(C_1-C_6)$alkyl, $(C_1-C_6)$alkoxy, trifluoromethyl, $(C_1-C_6)$ alkylthio, $(C_1-C_6)$alkylsulfonyl, acyl, $(C_1-C_6)$alkoxycarbonyl, carboxamido, $NR_{10}R_{11}$, $OSO_2NR_{10}R_{11}$ $NR_{12}SO_2NR_{10}R_{11}$ group.

A particularly preferred group of these compounds are those in which:
- one of $R_3$ and $R_8$ is hydroxy, cyano, $(C_1-C_6)$alkoxy or $OSO_2NR_{10}R_{11}$; and
- the other is hydrogen or a hydroxy, halogen, nitro, cyano, $(C_1-C_6)$alkoxy, $NR_{10}R_{11}$, $SO_2NR_{10}R_{11}$, $OSO_2NR_{10}R_{11}$, $NR_{12}SO_2NR_{10}R_{11}$, $OSO_2NR_{10}SO_2NR_{11}R_{12}$ group.

Preferably, the compounds of formula (I) are those in which:
- one of $R_3$ and $R_8$ is cyano; and
- the other is hydrogen or a hydroxy, halogen, nitro, $(C_1-C_6)$alkoxy, trifluoromethyl, $NR_{10}R_{11}$, $SO_2NR_{10}R_{11}$, $OSO_2NR_{10}R_{11}$, $NR_{12}SO_2NR_{10}R_{11}$ group.

Further preferred compounds are those in which:
- one of $R_4$ and $R_9$ is hydrogen or a hydroxy, cyano, $OSO_2NR_{10}R_{11}$ group; and
- the other is hydrogen or a hydroxy, cyano, halogen, nitro, $(C_1-C_6)$alkyl, $(C_1-C_6)$alkoxy, trifluoromethyl, $NR_{10}R_{11}$, $OSO_2NR_{10}R_{11}$, $CO_2R_{10}$, $CHO$, $NR_{12}SO_2NR_{10}R_{11}$ group.

Another group of preferred compounds are those in which:
- $R_4$ is hydrogen, hydroxy, cyano, or $OSO_2NR_{10}R_{11}$;
- $R_9$ is a hydrogen or a hydroxy, cyano, halogen, nitro, $(C_1-C_6)$alkyl, $(C_1-C_6)$alkoxy, trifluoromethyl, $NR_{10}R_{11}$, $OSO_2NR_{10}R_{11}$, $CO_2R_{10}$, CHO group.

Especially preferred compounds of formula (I) are those where:
- $R_4$ is hydrogen; and
- $R_9$ is a hydroxyl, cyano, halogen, nitro, $(C_1-C_6)$alkyl, $(C_1-C_6)$alkoxy, trifluoromethyl, $NR_{10}R_{11}$, $OSO_2NR_{10}R_{11}$, $CO_2R_{10}$, CHO or $NR_{12}SO_2NR_{10}R_{11}$ group.

Particularly preferred compounds of formula (I) are those in which Z is:

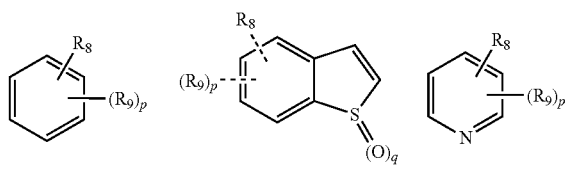

in which $R_8$ and $R_9$ are as hereinabove defined.

In the above defined compounds, $R_6$ and $R_9$ are preferably as follows:
- $R_5$ is hydrogen, hydroxy, halogen, nitro, cyano, $(C_1-C_6)$alkoxy, $NR_{10}R_{11}$, $SO_2NR_{10}R_{11}$, $OSO_2NR_{10}R_{11}$, $NR_{12}SO_2NR_{10}R_{11}$ or $OSO_2NR_{10}SO_2NR_{11}R_{12}$ group;
- $R_9$ hydrogen or a hydroxy, cyano, halogen, nitro, $(C_1-C_6)$alkyl, $(C_1-C_6)$alkoxy, trifluoromethyl, $NR_{10}R_{11}$, $OSO_2NR_{10}R_{11}$, $CO_2R_{10}$, CHO, $NR_{12}SO_2NR_{10}R_{11}$ group.

p and q are as defined above.

Among the compounds of formula (I), those in which Q is selected from a direct link, $C(O)$, $SO_2$, CONH, $C(O)(CH_2)_n$, $(CH_2)_n(O)$ or $(CH_2)_n$ in which n is 0, 1 or 2, are also particularly preferred.

Particularly preferred are the compounds of formula (II)

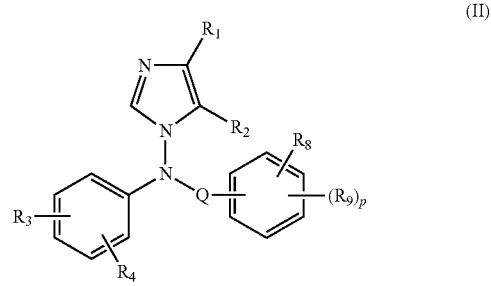

in which:
- Q is $(CH_2)_n$ in which n is 0, 1 or 2;
- one of $R_3$ and $R_8$ is a hydroxy, nitro, $NR_{10}R_{11}$, $OSO_2NR_{10}R_{11}$ or $NR_{12}SO_2NR_{10}R_{11}$ group and the other is hydrogen or a hydroxy, cyano, halogen, nitro, $(C_1-C_6)$alkyl, $(C_1-C_6)$alkoxy, trifluoromethyl, $(C_1-C_6)$alkylthio, $(C_1-C_6)$alkylsulfonyl, acyl, $(C_1-C_6)$alkoxycarbonyl, carboxamido, $NR_{10}R_{11}$, $OSO_2NR_{10}R_{11}$ or $NR_{12}SO_2NR_{10}R_{11}$ group;
- $R_4$ and $R_9$ are each independently hydrogen, hydroxy, cyano, halogen, nitro, $(C_1-C_6)$alkyl, $(C_1-C_6)$alkoxy, trifluoromethyl, $(C_1-C_6)$alkylthio, $(C_1-C_6)$alkylsulfonyl, acyl, $(C_1-C_6)$alkoxycarbonyl, carboxamido, $NR_{10}R_{11}$, $OSO_2NR_{10}R_{11}$ or $NR_{12}SO_2NR_{10}R_{11}$ group.
- $R_{10}$ and $R_{11}$ are each independently hydrogen, a $(C_1-C_6)$alkyl or a $(C_3-C_8)$cycloalkyl;
- p is 1, 2, 3 or 4;
- $R_8$ and $R_9$ together with the phenyl ring bearing them can also form a benzoxathiazine dioxide or a dihydrobenzoxathiazine dioxide;
- $R_3$ and $R_4$ together with the phenyl ring bearing them can also form a benzofurane or a N-methylbenzotriazole.

Among these compounds of formula (II), those which fulfil at least one of the following conditions are preferred:
- Q is $(CH_2)_n$ in which n 0, 1 or 2;
- $R_8$ is hydroxy, halogen, nitro, cyano or a $(C_1-C_6)$alkoxy, $NR_{10}R_{11}$ $SO_2NR_{10}R_{11}$, $OSO_2NR_{10}R_{11}$ or $NR_{12}SO_2NR_{10}R_{11}$ group;
- $R_9$ is hydrogen, hydroxy, cyano, halogen, nitro, $(C_1-C_6)$alkyl, $(C_1-C_6)$alkoxy, trifluoromethyl, $NR_{10}R_{11}$, $OSO_2NR_{10}R_{11}$;
- p is 1, 2, 3 or 4.

Most preferred compounds of formula (II) are those in which:
- n is 0 or 1;
- $R_1$ and $R_2$ are each independently hydrogen or $(C_1-C_6)$alkyl;
- $R_4$ and $R_9$ are each independently hydrogen, halogen, $(C_1-C_6)$alkoxy, acyl, $NR_{10}R_{11}$, $OSO_2NR_{10}R_{11}$ or $NR_{12}SO_2NR_{10}R_{11}$.

Especially preferred compounds of formula (II) are those in which:
- n is 0 or 1;
- $R_1$, $R_2$ and $R_4$ are each hydrogen;
- $R_9$ is hydrogen, halogen, $(C_1-C_6)$alkoxy or $OSO_2NR_{10}R_{11}$.

Particularly preferred compounds of formula (II) are those in which:
- n and p are 1;
- $R_8$ is a hydroxy, halogen, nitro, cyano, $(C_1-C_6)$alkoxy, $NR_{10}R_{11}$, $SO_2NR_{10}R_{11}$, $OSO_2NR_{10}R_{11}$, $NR_{12}SO_2NR_{10}R_{11}$, or $OSO_2NR_{10}SO_2NR_{11}R_{12}$ group;
- $R_9$ is a hydroxy, cyano, halogen, nitro, $(C_1-C_6)$alkyl, $(C_1-C_6)$alkoxy, trifluoromethyl, $NR_{10}R_{11}$, $OSO_2NR_{10}R_{11}$, $CO_2R_{10}$ or CHO group;

$R_3$ is cyano, hydroxy, $OSO_2NR_{10}R_{11}$ or $NR_{12}SO_2NR_{10}R_{11}$;

$R_4$ is hydrogen, hydroxy, halogen, cyano or $OSO_2NR_{10}R_{11}$.

Among these compounds, those which fulfil at least one of the following conditions are also preferred:

one of $R_3$ and $R_8$ is hydroxy, cyano or $OSO_2NR_{10}R_{11}$, preferably cyano or $OSO_2NR_{10}R_{11}$; and the other is hydroxy, nitro, $NR_{10}R_{11}$, $OSO_2NR_{10}R_{11}$ or $NR_{12}SO_2NR_{10}R_{11}$, preferably hydroxy or $OSO_2NR_{10}R_{11}$.

Among these compounds of formula (II), those wherein $R_{10}$ and $R_{11}$ are hydrogen are mostly preferred.

Particularly preferred are also the compounds of formula (III):

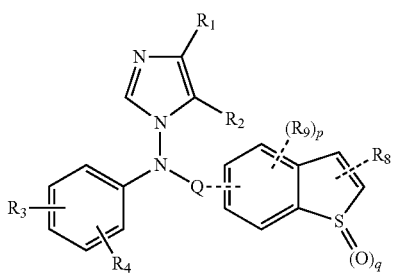

(III)

in which:

Q is $(CH_2)_m$—X—$(CH_2)_n$-A-;

A is a direct bond or O, S, SO; $SO_2$, $NR_5$;

X is a direct bond, $CF_2$, O, S, SO, $SO_2$, C(O), $NR_5$ or $CR_6R_7$;

m and n are each independently 0, 1, 2, 3 or 4;

$R_3$, $R_4$, $R_8$ and $R_9$ are each independently hydrogen or a hydroxy, cyano, halogen, nitro, $(C_1$-$C_6)$alkyl, $(C_1$-$C_6)$alkoxy, benzyloxy, trifluoromethyl, $(C_1$-$C_6)$alkylthio, $(C_1$-$C_6)$alkylsulfonyl, acyl, $(C_1$-$C_6)$alkoxycarbonyl, $NR_{10}R_{11}$, $OPO(OR_{10})_2$, OCHO, $COOR_{10}$, $SO_2NR_{10}R_{11}$, $OSO_2NR_{10}R_{11}$, $SO_2OR_{10}$, $OSO_2OR_{10}$, $SSO_2NR_{10}R_{11}$, $CONR_{10}R_{11}$, $OCONR_{10}R_{11}$, $OCSNR_{10}R_{11}$, $SCONR_{10}R_{11}$, $SCSNR_{10}R_{11}$, $NR_{12}SO_2NR_{10}R_{11}$, tetrazolyl, $NR_{10}CONR_{11}OH$, $NR_{10}SO_2NR_{11}OH$, NOH—CHO, $NOHSO_2NR_{10}R_{11}$, or $OSO_2NR_{10}OH$ group;

p is 0, 1 or 2.

$R_5$, $R_6$, $R_7$, $R_{10}$, $R_{11}$ and $R_{12}$ are each independently hydrogen, a $(C_1$-$C_6)$alkyl or a $(C_3$-$C_6)$cycloalkyl; $R_{10}$ can also be a salt; $R_{10}$ and $R_{11}$ can also form, together with the nitrogen atom to which they are bound, a 5- to 7-membered heterocycle containing one or two heteroatoms selected from O, S and N;

The dotted line means that Q and/or $R_8$ and/or $R_9$ can be on any position of the benzothiophene ring.

Among the compounds of formula (III) those which fulfil at least one of the following condition are also preferred:

$R_3$ is hydrogen, halogen or cyano;

$R_8$ is $OSO_2NR_{10}R_{11}$ or $NR_{12}SO_2NR_{10}R_{11}$;

$R_9$ is hydrogen, halogen, nitro, $COOR_{10}$ or cyano;

$R_4$ is hydrogen, halogen, cyano, $(C_1$-$C_6)$alkoxy, $NR_{10}R_{11}$, $OSO_2NR_{10}R_{11}$ or $NR_{12}SO_2NR_{10}R_{11}$;

$R_{10}$, $R_{11}$ and $R_{12}$ are each independently hydrogen or $(C_1$-$C_6)$alkyl.

The compounds of formula (III), wherein Q is $(CH_2)_m$—X—$(CH_2)_n$-A where m is 0, 1 or 2 and X is a direct bond, $SO_2$ or CO, n is 0 and A is a direct bond are also preferred.

Particularly preferred are the compounds of formula (IV):

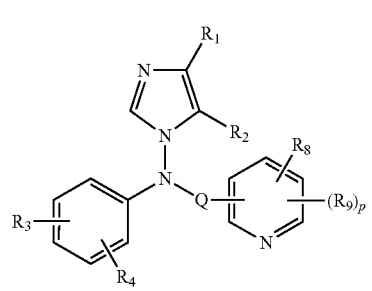

(IV)

in which $R_1$, $R_2$, $R_3$, $R_4$, $R_8$, $R_9$ and p are as defined for compounds of formula (I).

Particularly preferred compounds of formula (IV) are those in which:

$R_3$ is cyano or $OSO_2NR_{10}R_{11}$;

$R_4$ is hydrogen, hydroxyl, halogen, cyano, $OSO_2NR_{10}R_{11}$;

$R_9$ is hydroxy, cyano, $OSO_2NR_{10}R_{11}$, $NR_{10}R_{11}$, $NR_{12}SO_2NR_{10}R_{11}$, OCHO, tetrazolyl;

$R_9$ is hydrogen, halogen, nitro, cyano or $CO_2R_{10}$; and

Q is as defined above for compounds of formula (I).

By virtue of their capability to inhibit the enzymes aromatase and/or steroid sulfatase and/or carbonic anhydrase, the compounds of the present invention can be used alone or in combination with other active ingredients for the treatment or the prevention of any hormone or non hormone-dependent cancer, in humans as well as in wild or domestic animals. Because of their inhibition activity of aromatase and/or steroid sulfatase, the compounds of the invention are suitable for the management of estrogen-regulated reproductive functions, in humans as well as in wild or domestic animals.

In the treatment or prevention of the above conditions, the compounds of the invention can be used alone or in combination with an antiestrogen, a SERM (selective estrogen receptor modulator), an aromatase inhibitor, a carbonic anhydrase inhibitor, an antiandrogen, a steroid sulfatase inhibitor, a lyase inhibitor, a progestin, or a LH-RH agonist or antagonist. The compounds of the invention can also be used in combination with a radiotherapeutic agent; a chemiotherapeutic agent such as a nitrogenated mustard analogue like cyclophosphamide, melphalan, iphosphamide, or trophosphamide; an ethylenimine like thiotepa; a nitrosourea like carmustine; a lysed agent like temozolomide or dacarbazine; an antimetabolite of folic acid like methotrexate or raltitrexed; a purine analogue like thioguanine, cladribine or fludarabine; a pyrimidine analogue like fluorouracil, tegafur or gemcitabine; an alkaloid of vinca or analogue like vinblastine, vincristine or vinorelbine; a podophyllotoxin derivative like etoposide, taxanes, docetaxel or paclitaxel; an anthracycline or analogue like doxorubicin, epirubicin, idarubidn or mitoxantrone; a cytotoxic antibiotic like bleomycin or mitomycin; a platinum compound like cisplatin, carboplatin or oxaliplatin; a monoclonal antibody like rituximab; an antineoplastic agent like pentostatin, miltefosine, estramustine, topotecan, irinotecan or bicalutamide; or with a prostaglandin inhibitor (COX 2/COX 1 inhibitor).

The compounds of the invention can also be used for the control or management of estrogen-regulated reproductive functions such as male or female fertility, pregnancy, abortion or delivery, in humans as well as in wild or domestic animal species, alone or in combination with one or several other therapeutic agents such as a LH-RH agonist or antagonist, an estroprogestative contraceptive, a progestin, an antiprogestin or a prostaglandin inhibitor.

Breast tissue being a sensitive target of estrogen-stimulated proliferation and/or differentiation, inhibitors of aromatase and/or steroid sulfatase and/or carbonic anhydrase can be used in the treatment or prevention of benign breast diseases in women, gynecomastia in men and in benign or malignant breast tumors with or without metastasis both in men and women or in male or female domestic animals. The compounds of the invention can also be used in the treatment or prevention of benign or malignant disease of the uterus or the ovary. In each case, the compounds of the invention can be used alone or in combination with one or several other sexual endocrine therapeutic agents such as an antiandrogen, an anti-estrogen, a progestin or a LH-RH agonist or antagonist.

As the enzyme steroid sulfatase transforms DHEA sulfate into DHEA, a precursor of active androgens (testosterone and dihydrotestosterone), the compounds of the invention can be used in the treatment or prevention of androgen-dependent diseases such as androgenic alopecia (male pattern loss) (Hoffman R et al., J. Invest. Dermatol., 2001, 117, 1342-1348), hirsutism, acne (Billich A et al., WO 9952890), benign or malignant diseases of the prostate or the testis (Reed M J, Rev. Endocr., Relat. Cancer, 1993, 45, 51-62), alone or in combination with one or several other sexual endocrine therapeutic agents such as an antiandrogen, an antiestrogen, a SERM, an antiaromatase, a progestin, a lyase inhibitor or a LH-RH agonist or antagonist.

Inhibitors of steroid sulfatase are also potentially involved in the treatment of cognitive dysfunction, because they are able to enhance learning and spatial memory in the rat (Johnson D A, Brain Res, 2000, 865, 286-290). DHEA sulfate as a neurosteroid affects a number of neurotransmitter systems including those involving acetylcholine, glutamate, and GABA, resulting in increased neuronal excitability (Wolf O T, Brain Res. Rev, 1999, 30, 264-288). The compounds of the present invention are thus also useful for enhancing the cognitive function, especially for the treatment of senile dementia, including Alzheimer's diseases, by increasing the DHEA levels in the central nervous system.

In addition, estrogens are involved in the regulation of the balance between $Th_1$ and $Th_2$ predominant immune functions and may therefore be useful in the treatment or prevention of gender-dependent auto-immune diseases such as lupus, multiple sclerosis, rheumatoid arthritis and the like (Daynes R A, J. Exp. Med, 1990, 171, 979-996). Steroid sulfatase inhibition was further shown to be protective in models of contact allergy and collagen-induced arthritis in rodents (Suitters A J, Immunology, 1997, 91, 314-321).

Studies using 2-MeOEMATE have shown that steroid sulfatase inhibitors have potent estradiol-independent growth-inhibitory effect (MacCarthy-Moorogh L, Cancer Research, 2000; 60, 5441-5450). A decrease in tumor volume was surprisingly observed with the compounds of the invention, with low tumor steroid sulfatase inhibition. In view of this, the compounds of the invention could lead to a decrease in cellular division because of the large interaction between such new chemical entities and the microtubular network within the cancerous cell, whatever the tissue, including breast, endometrium, uterus, prostate, testis or metastasis generated therefrom. The compounds of the invention could therefore be useful in the treatment of non-estrogen dependent cancer.

The compounds of the invention are of particular value for the treatment or prevention of estrogen-dependent diseases or disorders, i.e. estrogen-induced or estrogen-stimulated diseases or disorders (Golob T, Bioorg. Med. Chem., 2002, 10, 3941-3953).

In addition, the compounds of the present invention are inhibitors of carbonic anhydrase (CA). This property could explain the interest of such compounds in non-hormone-dependent cancer. Immunohistochemical studies of CA II have shown that it is expressed in malignant brain tumors (Parkkila A-K. et al., Histochem. J., 1995, 27: 974-982) and gastric and pancreatic carcinomas (Parkkila S et al., Histochem. J., 1995, 27: 133-138), and recent evidence has shown that CA IX and XII are also expressed in some tumors and may be functionally related to oncogenesis. Ivanov et al. (Proc. Natl. Acad. Sci. USA, 1998, 95: 12596-12601) recently hypothesized that tumor-associated CA IX and XII may be implicated in acidification of the extracellular medium surrounding cancer cells, which would create a microenvironment conducive to tumor growth and spreading. It has been shown that acetazolamide markedly inhibited invasion capacity in four renal cancer cell lines (Parkkila S et al., Proc. Natl. Acad. Sci. USA, 2000, 97: 2220-2224), an effect attributable to CA II, IX, and XII, which were expressed in these cells. Leukemia cells can easily spread from bone marrow to other organs via circulation, but various leukemias differ in their ability to form extramedullary tumors i.e., metastases. If CA activities were essential for invasion by other cancer cells, one could analogously predict that active CA(s) could also function in leukemia cells.

As used herein, the term "combined" or "combination" refers to any protocol for the co-administration of a compound of the invention and one or more other pharmaceutical substances, irrespective of the nature of the time of administration and the variation of dose over time of any of the substances. The co-administration can for example be parallel, sequential or over a period of time.

For the treatment/prevention of any of the above-mentioned diseases or disorders, the compounds of the invention may be administered, for example, orally, topically, parenterally, in dosage unit formulations containing conventional non-toxic pharmaceutically acceptable carriers, adjuvants and vehicles. These dosage forms are given as examples, but other dosage forms may be developed by those skilled in the art of formulation, for the administration of the compounds of the invention. The term parenteral as used herein includes subcutaneous injections, intravenous, intramuscular, intrasternal injection or infusion techniques. In addition to the treatment of humans, the compounds of the invention are effective in the treatment of warm-blooded animals such as mice, rats, horses, cattle sheep, dogs, cats, etc.

The pharmaceutical compositions containing the active ingredient(s) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient(s) in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic add or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

They may also be coated by the technique described in the U.S. Pat. Nos. 4,256,108; 4,166,452 and 4,265,874 to form osmotic therapeutic tablets for controlled release.

Formulations for oral use may also be presented as hard gelatin capsules wherein the active ingredient(s) is (are) mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active ingredient(s) in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty adds, for example polyoxyethylene stearate, or condensation products of ethylene oxide with long chain aliphatic alcohols, for example heptadecaethyleneoxycetanol, or condensation products of ethylene oxide with partial esters derived from fatty adds and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient(s) in a vegetable oil, for example peanut oil, olive oil, sesame oil or coconut oil, or in mineral oil such as liquid paraffin. The oily suspensions may contain a thickening agent, for example beeswax, hard paraffin or acetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient(s) in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present. The pharmaceutical compositions of the invention may also be in the form of an oil-in-water emulsion. The oily phase may be a vegetable oil, for example olive oil or peanut oil, or a mineral oil, for example liquid paraffin or mixtures of these. Suitable emulsifying agents may be naturally occurring phosphatides, for example soybean, lecithin, and esters or partial esters derived from fatty adds and hexitol anhydrides, for example sorbitan monooleate, and condensation products of the said partial esters with ethylene oxide, for example polyoxyethylene sorbitan monooleate. The emulsions may also contain sweetening and flavouring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage levels of the order of from about 0.0001 mg to about 20 mg/kg of body weight per day are useful in the treatment of the above-indicated conditions, or alternatively about 0.1 mg to about 2000 mg per patient per day.

The amount of active ingredient that may be combined with the carrier materials to produce a single dosage form will vary depending upon the host treated and the particular mode of administration. Dosage unit forms will generally contain between from about 0.1 mg to about 400 mg of compound of the invention, typically 0.1 mg, 1 mg, 2 mg, 5 mg, 10 mg, 20 mg, 40 mg, 80 mg, 100 mg, 200 mg or 400 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

According to another object, the invention relates to a method for the treatment or prevention of the above-mentioned diseases, disorders or conditions. The method comprises administering to a subject (human or animal) in need thereof a therapeutically effective amount of a compound of the invention or a pharmaceutically acceptable add addition salt thereof.

The 1-N-aryl-amino-1H-imidazole derivatives of formula (I) and their add addition salts can be prepared following general schemes I a, I b, IIa, IIb, III, IV and V in which $(\ )_m$ represents $(CH_2)_m$ and $(\ )_n$ represents $(CH_2)_n$.

Scheme Ia

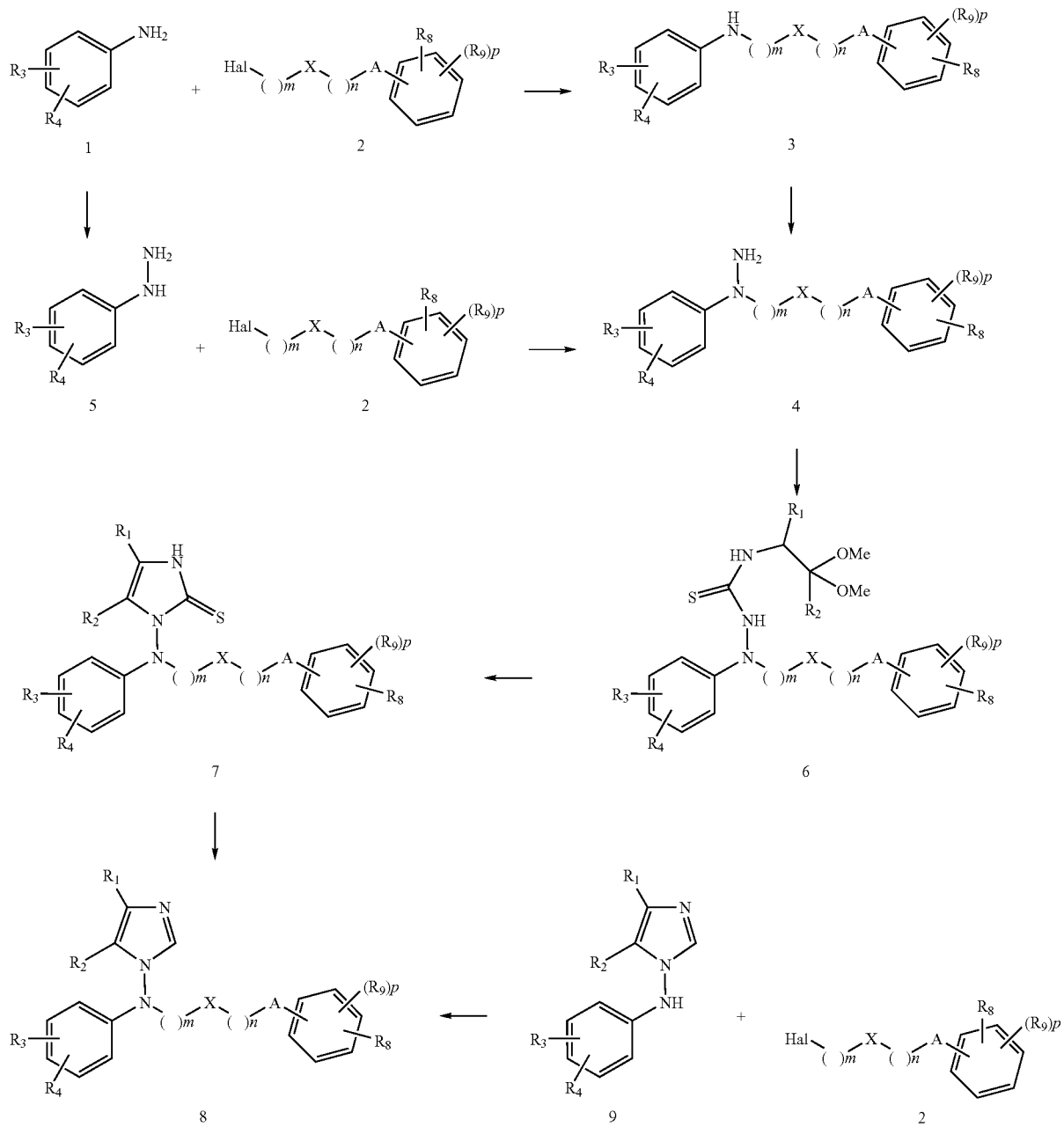

According to scheme I a, N,N-disubstituted aniline (3) can be obtained by condensation of the aniline derivative (1) with halogeno derivatives, alcoyl derivatives, sulfonyl derivatives or sulfinyl derivatives (2) using standard conditions (March J., *Advanced Organic Chemistry*, Fourth edition, Wiley Interscience, New-York). Most of the halogeno derivatives, alcoyl derivatives, sulfonyl derivatives or sulfinyl derivatives (2) are commercially available or are synthesized by usual chemistry methods (see experimental part).

Compound (3) is converted to its nitroso derivative using standard conditions, then reduced to afford the 1,1-disubstituted hydrazine of formula (4). Alternatively, the 1,1-disubstituted hydrazine (4) can be prepared by selective N-alkylation of a hydrazine of formula (5) with a compound of formula (2) using the conditions described by U. Lerch and J. König (*Synthesis*, 1983, 2, 157-8) or the conditions described by J. Chung et al. (*Tetrahedron Letters*, 1992, 33, 4717-20). Then, condensation of (4) with a dialkyloxy-alkyl-isothiocyanate derivative or an ethylenedioxy-alkyl-isocyanate derivative, affords the thiosemicarbazide (6) which is transformed to the 1-amino-imidazole-2-thione (7) by treatment with an acid like acetic acid or sulphuric acid.

Desulfurization of (7) in acetic acid, following the conditions described by S. Grivas and E. Ronne in *Acta Chemica Scandinavia*, 1995, 49, 225-229, gives the final 1-N-phenyl-amino-1H-imidazole (8), which is optionally converted to one of its acid addition salts.

Alternatively said compounds (8) where $R_3$ or $R_4$ is an electron-withdrawing group can be obtained by condensation of the N-imidazoloaniline (9) with halogeno derivatives, alcoyl derivatives, sulfonyl derivatives or sulfinyl derivatives (2) using standard conditions (March J., *Advanced Organic Chemistry*, Fourth edition, Wiley Interscience, New-York).

If $R_8$ is ester, saponification of compound (8) gives carboxylic derivative by usual chemistry methods.

If $R_8$ is sulfamide, it can be directly obtained with correct substituted alcoyl derivative or halogeno derivative (2).

If $R_8$ is cyano group, reaction with sodium azide gives tetrazolyl group (Kiyoto K., *Synthesis*, 1998, 910-14).

The compound (9) is obtained by a process similar to the process disclosed herein above for obtaining the compound (8) starting from the compound (4).

These compounds are transformed into the corresponding sulfamates (11) or aminosulfonylamines (13) by treatment with sodium hydride and sulfamoyl chloride (Nussbaumer. P, *J Med Chem*, 2002, 45, 4310-20) or by reaction with sulfamoyl chloride in dimethylacetamide (DMAc) (Makoto O, *Tetrahedron letters*, 2000, 41, 7047-51).

These hydroxyl compounds can be transformed into formate derivatives by treatment with formyl acetate (Schreiner E., *Bioorg Med Chem Lett*, 2004, 14, 4999-5002) or into 1H-imidazole-1-carboxylate derivatives by treatment with N,N'-carbonyldiimidazole (Fischer, W., *Synthesis*, 2002, 1, 29-30) Compounds (10) or (12) having both an

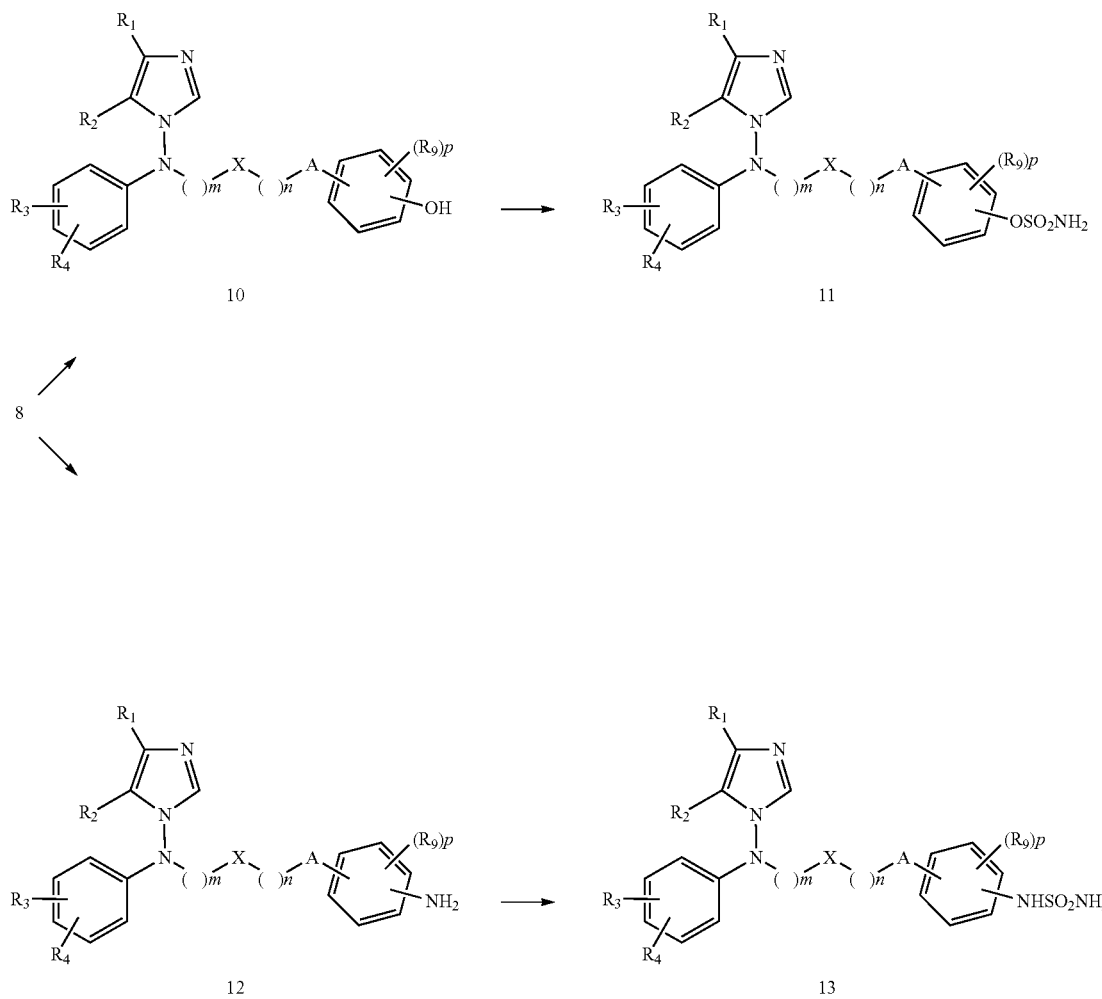

Scheme Ib

According to scheme Ib deprotection of methoxy or benzyloxy derivatives (8) with tribromoborane (McOmie. J. F. W, *Tetrahedron*, 1968, 24, 2289-92) or piperidine (Nishioka H. Synthesis, 200, 2, 243-46) or by hydrogenation (Felix A., *J Org Chem*, 1978, 43, 4194-97) gives the hydroxyl compound (10). Reduction of nitro compound (8) by stannous chloride or with ruthenium and hydrazine (WO 02051821) gives amino-compound (12) (Matassa V., *J Med Chem*, 1990, 33, 2621-29).

amino and an hydroxyl in an ortho position, can be transformed to the corresponding benzoxathiazoles following the conditions proposed by K. K. Andersen (*J Org Chem*, 1991, 56, 23, 6508-6516). When X is CO or CS, reduction of ketone, thioketone, amide, thioamide is performed following standard conditions (March J., *Advanced Organic Chemistry*, Fourth edition, Wiley Interscience, New-York). These reduction steps can be effective at any steps of synthesis process.

Scheme IIa

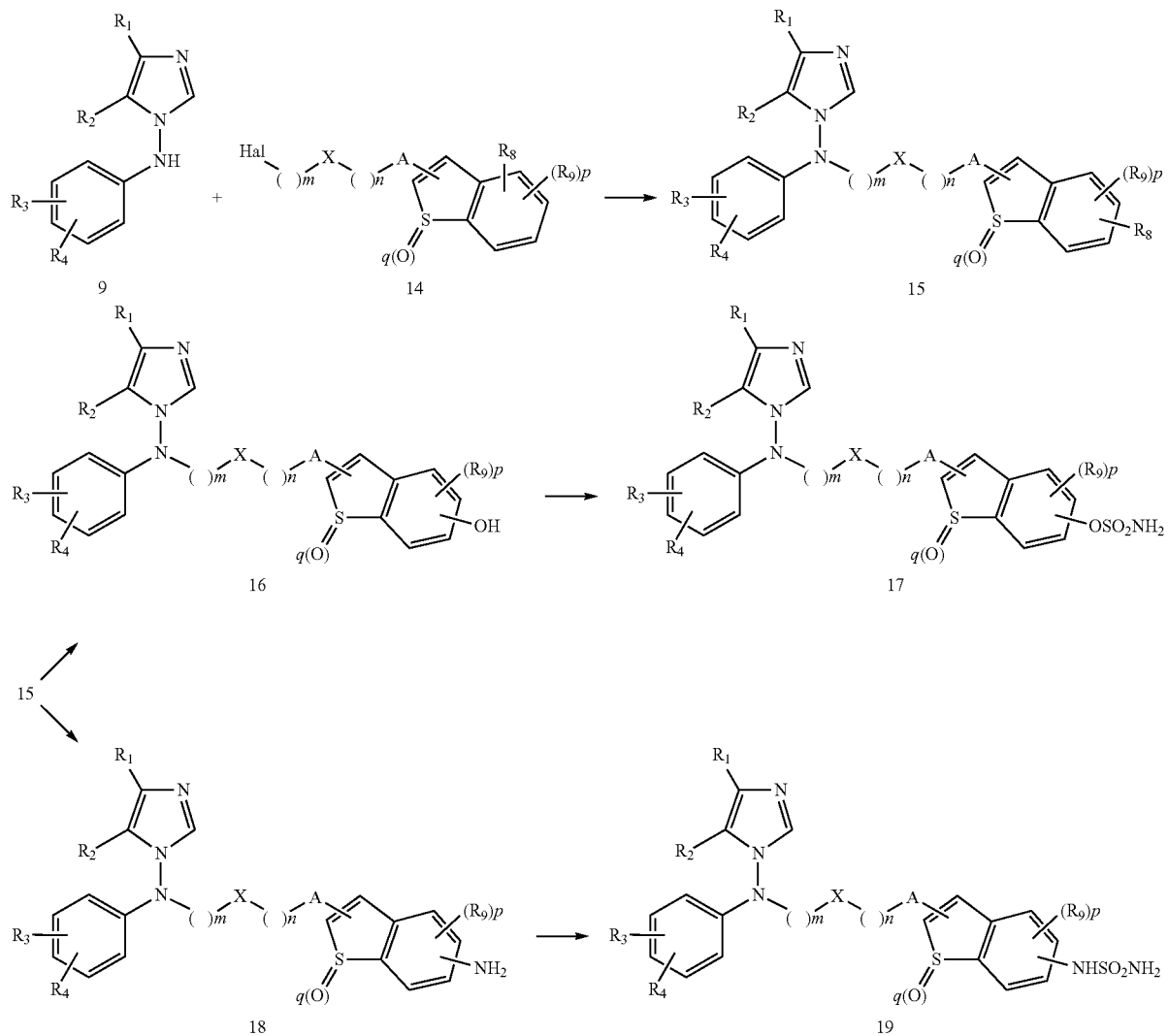

According to scheme IIa, compounds (15) can be obtained by the same procedure as compound (3) in scheme Ia starting from compounds (1) and (14) or by condensation of the N-imidazoloaniline (9) with halogeno derivatives, alcoyl derivatives, sulfonyl derivatives or sulfinyl derivatives (14) using standard conditions (March J., *Advanced Organic Chemistry*, Fourth edition, Wiley Interscience, New-York). Most of the halogeno derivatives, alcoyl derivatives, sulfonyl derivatives or sulfinyl derivatives (14) are commercially available or are synthesized by usual chemistry methods (see experimental part).

If $R_8$ is ester, saponification of compound (15) gives carboxylic derivative by usual chemistry methods.

If $R_8$ is sulfamide, it can be directly obtained with correct substituted alcoyl derivative or halogeno derivative (14).

If $R_8$ is cyano group, reaction with sodium azide gives tetrazolyl group (Kiyoto K., *Synthesis*, 1998, 910-14).

Deprotection of methoxy or benzyloxy benzothiophene (15) with tribromoborane (McOmie. J. F. W, *Tetrahedron*, 1968, 24, 2289-92) or by hydrogenation (Felix A., *J Org Chem*, 1978, 43, 419-497) gives the hydroxy benzothiophene (16).

Reduction of nitro benzothiophene compound (15) by stannous chloride gives amino-benzothiophene (18) (Matassa V., *J Med Chem*, 1990, 33, 2621-29).

These compounds (16) and (18) are transformed into the corresponding sulfamates (17) or aminosulfonylamines (19) using the same conditions as for the synthesis of compounds (11) or (13).

Oxidation of sulphur on benzothiophene by hydrogen peroxide in trifluoroacetic acid, following the conditions described by Grivas S. and Ronne E. (*Acta Chemica Scandinavia*, 1995, 49, 225-229) or by meta-chloro-per-benzoic acid in methylene chloride gives the oxydised benzothiophenes. (Ong H. H., J Med Chem, 1987, 30, 12, 2295-2303).

Reduction of amide, thioamide, ketone, thioketone when X is CO or CS or reduction of oxidised sulphur function is performed following the conditions described by Ellefson C. (*J Med Chem*, 1981, 24, 1107-10), Hajos J. (*Complex Hydrides*, Elsevier, New York, 1979) or Drabowicz S. (*Org Prep Proceed Int*, 1977, 9, 63-83) and Bordwell J. (*J Am Chem Soc*, 1951, 73, 2251-53) or following standard conditions (March J., *Advanced Organic Chemistry*, Fourth edition, Wiley Interscience, New-York). These oxidation and reduction steps can be effective at any steps of synthesis process.

(Cannizzo S., *J Heterocyclic Chem*, 1990, 27, 2175-79) and by reduction of 2-nitro benzothiophene compound (21) by stannous chloride (Matassa V, *J Med Chem*, 1990, 33, 2621-29).

Scheme IIb

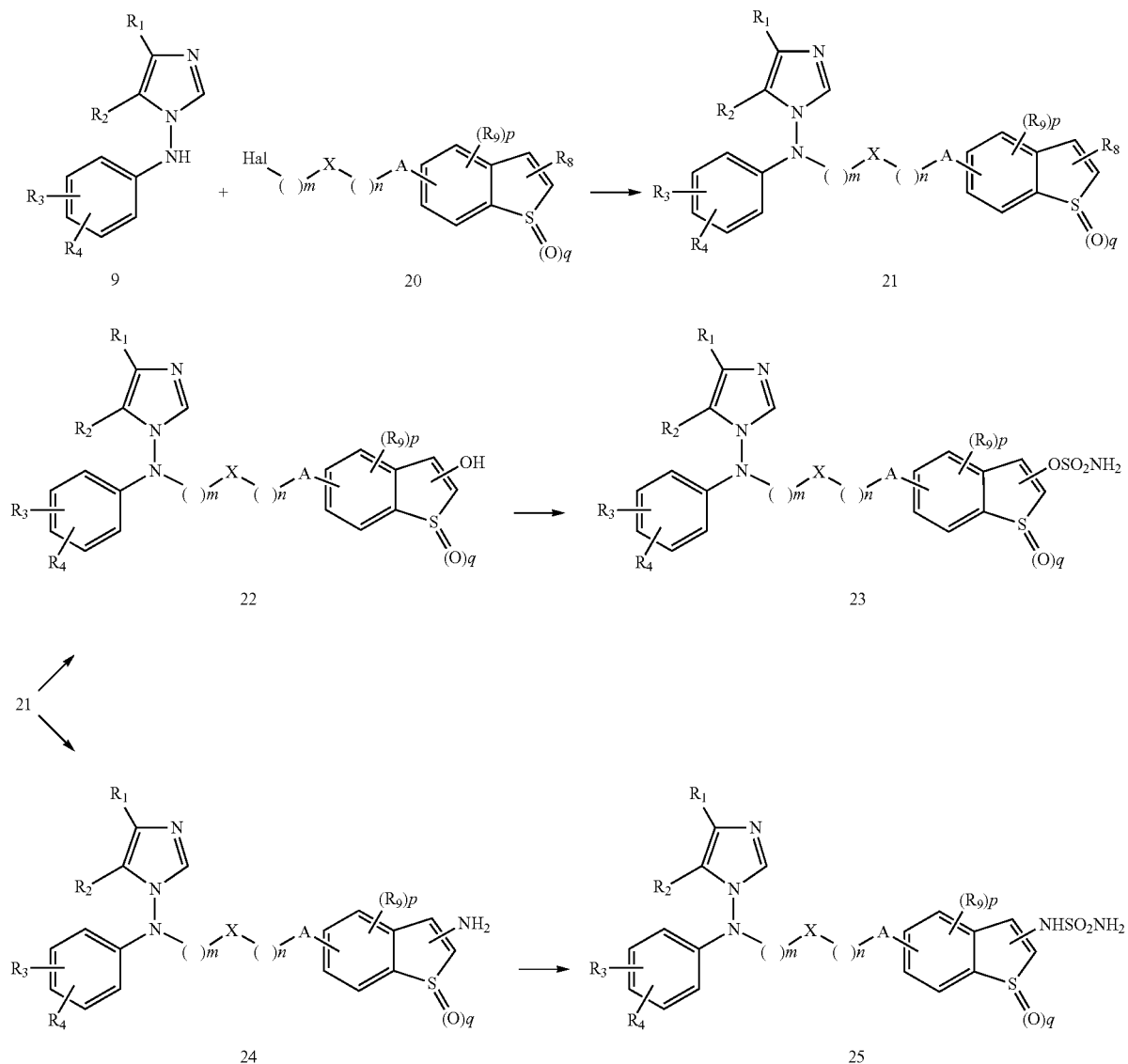

According to scheme IIb, compounds (21) are synthesized following the same synthetic methods as for compounds (3) starting from compounds (1) and (20) or (9) and (20).

3-Halogeno benzothiophene derivative (21) treated by aqueous metal hydroxide (Svoboda J., *Collect Czech Chem comm*, 2000, 65, 7, 1082-92 or Sall D., *J Med Chem*, 2000, 43, 4, 649-63) gives 3-hydroxy benzothiophene derivative (22) or treated by aqueous ammonia in acetone or ethanol (Bordwell F., *J. A. C. S.*, 1948, 70, 1955-58) gives 3-amino benzothiophene derivative (24). 2-Hydroxy benzothiophene derivative (22) or 2-amino benzothiophene derivative (24) are performed respectively by deprotection of 2-methoxy benzothiophene derivative (21) with pyridine hydrochloride These compounds (22) and (24) can be sulfamoylated to give (23) and (25) using the same conditions as for the synthesis of compounds (11) or (13).

Deprotonation of 2-H-benzothiophene derivative (21) with lithium amides or alkyls leads to lithiation at C-2 position. Addition of sulfuryl chloride yields chlorosulfonyl compound that is treated by aqueous ammonia in acetone (Graham S., *J Med Chem*, 1989, 32, 2548-54) to give 2-sulfonamide benzothiophene derivative (21) or addition of dry ice followed by hydrolysis gives 2-carboxylic acid benzothiophene derivative (21) (Matecka D., *J Med Chem*, 1997, 40, 705-16).

3-Carboxylic or carboxamide benzothiophene derivative (21) is prepared by treatment of 3-H-benzothiophene derivative with trichloroacetyl chloride/aluminium chloride followed by hydrolysis with water (Bonjouldian R., *Synth Comm*, 1985, 15, 8, 711-13) or aqueous ammonia (Tumbull K., *J Heterocycl Chem*, 2000, 37, 2, 383-88).

3-Sulfonamide derivative (21) is prepared following the conditions described by Chapman N. (*J. Chem. Soc.*, 1970, 18, 2431-35) or Hageman W. (Ger. Offen., 3435173, 11 Apr. 1985).

Oxidation of sulfur on benzothiophene and reduction of carboxamide, thioamide, ketone, thioketone, oxydised sulphur function can be performed at any step of synthesis following the same conditions already presented in this description.

According to scheme III, compounds (27) are obtained by condensation of the N-imidazoloaniline (9) with isocyanate derivatives (26) using standard conditions (March J., *Advanced Organic Chemistry*, Fourth edition, Wiley Interscience, New-York). Most of the isocyanate derivatives. (26) are commercially available or are synthesized by usual chemistry methods.

Compounds (28) and (30) are synthesized following the same synthetic methods as for compounds (10) and (12) in scheme Ib.

Compounds (29) and (31) are synthesized following the same synthetic methods as for compounds (11) and (13) in scheme Ib.

Scheme III

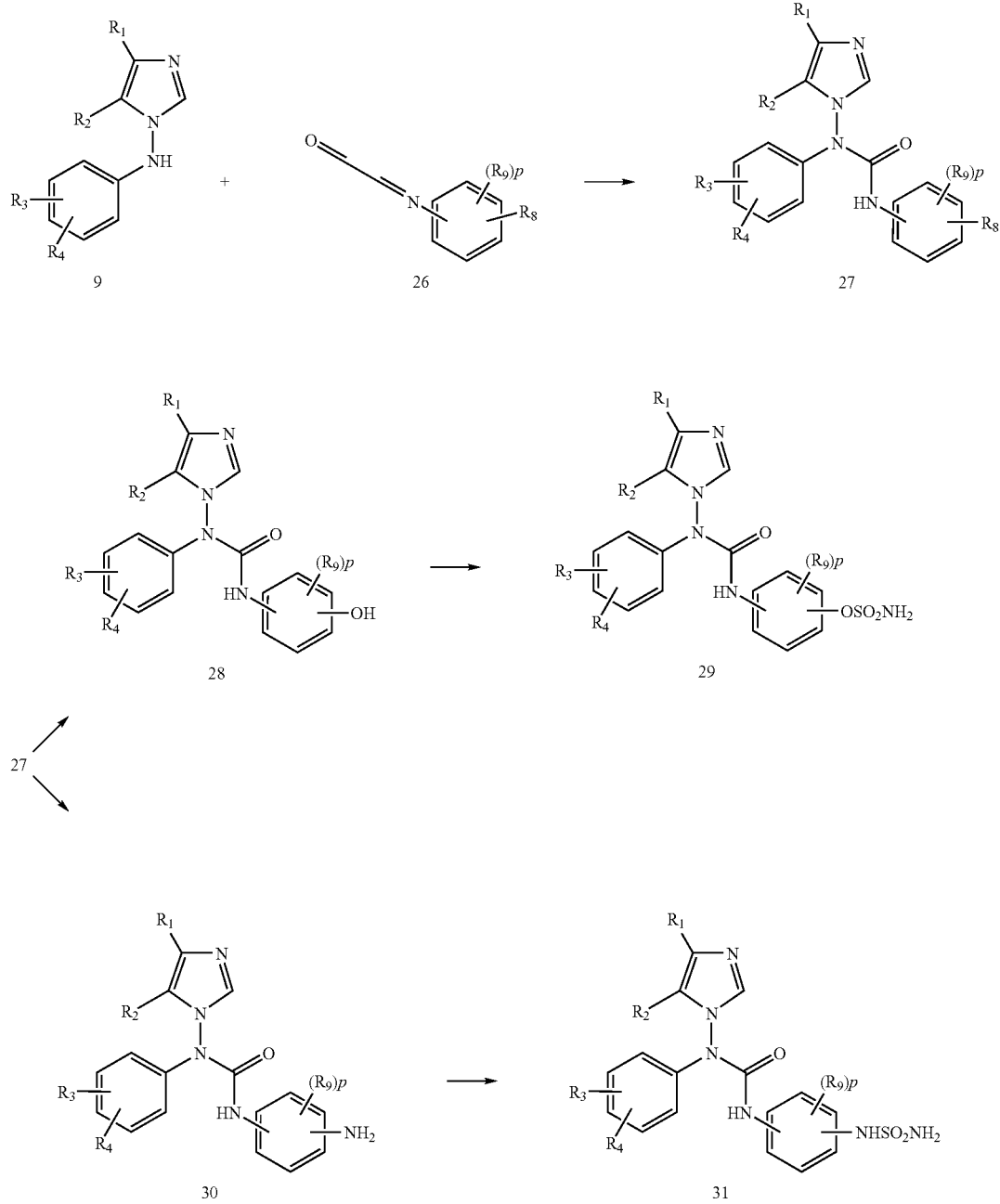

Scheme IV

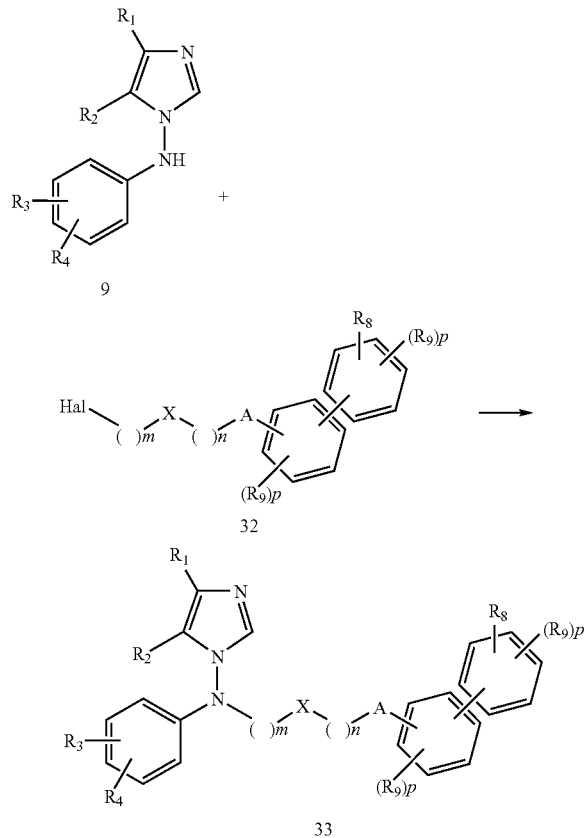

According to scheme IV, bi-aryl compounds (33) can be synthesized following the same synthetic methods as for compounds (8) with derivatives (32). Derivatives (32) are commercially available or synthesized by usual chemistry methods (as ex Buraway S, J Chem Soc, 1955, 2557; Tilley J W, J Med Chem, 1989, 32, 8, 1814).

Scheme V

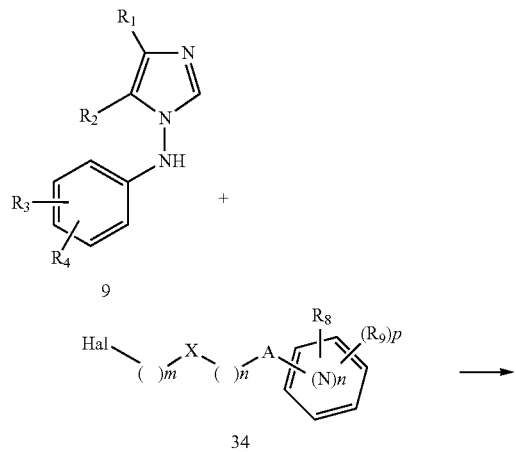

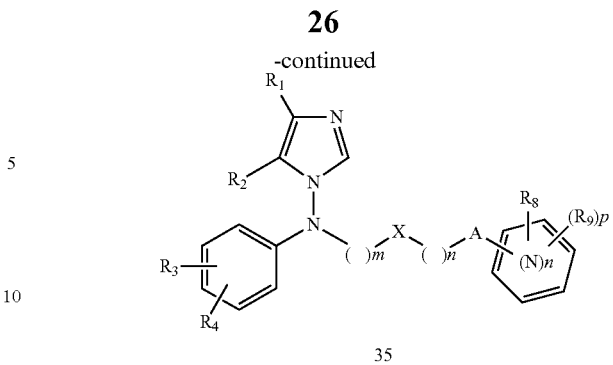

According to scheme V, compounds (35) are synthesized following the same synthetic methods as for compounds (8) with heterocycles (34) (one or two nitrogen atoms in any positions). Heterocycles (34) are commercially available or synthesized by usual chemistry methods (see following examples). Halogeno pyridine derivatives (34) can be obtained following publications (Biorg Med Chem Lett, 1996, 6, 21, 2613; Myers A G, J Org Chem, 1996, 61, 813; Tetrahedron, 1993, 49, 19, 4085) or from carboxylic acid (WO 0177078). Halogeno pyrimidine derivatives (34) can be obtained from alkyl pyrimidines (Budesinsky, Collect, Czech, Chem Commun, 1968, 33, 7, 2266; Kunieda T, J Am Chem Soc, 1971, 93, 3487) by usual halogenation (Isoda S, Chem pharm Bull, 1980, 28, 5, 1408; March J., *Advanced Organic Chemistry*, Fourth edition, Wiley Interscience, New-York), or from carbaldehydes (Bredereck, Chem Ber, 1967, 100, 11, 3664; Adams J L, Bioorg Med Chem Lett, 1998, 8, 22, 3111), and carboxylic acids (Huffman K R, J Org Chem, 27, 1962, 551; Daves J Org Chem, 1961, 26, 2755) can be transformed to acid chlorides (34). Halogeno pyrazine derivatives (34) can be obtained from alkyl pyrazines (Lutz W B, J Org Chem, 1964, 29, 415) by bromination, or from carbaldehydes (U.S. Pat. No. 3,558,625), and carboxylic acids (Sato N, J Heterocycl Chem, 19, 1982, 407-408; Felder P, Helv Chim Acta, 1964, 47, 873) can be transformed to add chlorides (34). Halogeno pyridazine derivatives (34) can be obtained following Piras S (Farmaco, 1993, 48, 9, 1249) Yanal, (Heterocycles, 1976, 4, 1331), or by halogenation of alkyl pyridazines (Becker, J Prakt Chem, 1970, 312, 591; DE 1950491) and carboxylic acids (Boger D L, J Am Chem Soc 1987, 109, 9, 2717) can be transformed to acid chlorides (34).

For all schemes IIa, IIb, III, IV, V, carboxylate derivative, sulfamide derivative and tetrazole derivative are synthesized by the methods already described for scheme Ia and R8 and (R9)$_p$ are performed following the same conditions already presented in this description.

The groups described for $R_3$, $R_4$, $R_8$ and $R_9$ can be obtained by usual chemistry methods (for references see review on sulfatase (Nussbaumer P, *Medecinal Research*, 2004, 24, 4, 529-76), on carbonic anhydrase (Supuran C T, *Carbonic anhydrase*, 2004, C R C press) and articles from Park J D (*J Heterocycl Chem*, 2000, 37, 2, 383-88), Schreiner E P (*Bioorg Med Chem Lett*, 2004, 14, 4999-5002) and Taylor S D (*Bioorg Med Chem Lett*, 2004, 14, 151-155).

The following examples are intended to illustrate and not to limit the scope of the invention.

Preparation of N,N-Disubstituted Hydrazines (4)

EXAMPLE 1

$N^1$-(4-yanophenylmethyl)-$N^1$-(4-methoxyphenyl) hydrazine

Chloromethylbenzonitrile (25 g, 164.90 mmol) was introduced with stirring into a flask containing toluene (200 ml)

and triethylamine (46.40 ml, 329.80 mmol). 4-methoxy-phenylhydrazine hydrochloride (28.80 g, 164.90 mmol) was added portionwise and the reaction mixture was stirred 3 h at reflux. After cooling, the mixture was filtered, washed with toluene (50 ml) and with water (200 ml) to give a white solid (27.20 g, 65%), mp: 115° C.

$^1$H-NMR (DMSO d$_6$): 3.65 (s, 3H), 4.30 (s, 2H), 4.57 (s, 2H), 6.77 (d, 2H), 6.94 (d, 2H), 7.48 (d, 2H), 7.76 (d, 2H).

Preparation of Imidazoles (9)

EXAMPLE 2

4-[N-(1H-imidazol-1-yl)amino]benzonitrile a) 4[N-(2,3-dihydro-1H-imidazol-1-yl-2-thione)amino]benzonitrile To a suspension of 4-cyanophenylhydrazine hydrochloride (6.00 g, 35.40 mmol) in ethanol (60 ml) was added dropwise 2,2-dimethoxyethylisothiocyanate (6.25 g, 42.4 mmol) and the reaction mixture was heated to reflux for 2 h. After cooling the solvent was evaporated under vacuum, the resulting oil was diluted with acetic acid/water (9/1, 32 ml) and the suspension was heated to reflux for 1.5 h and at room temperature overnight. The resulting residue was poured into water (300 ml) and a brown precipitate was collected. After trituration from ethanol, the brown solid afforded a white solid (4.60 g, 58%).

$^1$H-NMR (DMSO d$_6$): 6.54 (d, 2H), 7.00 (t, 1H), 7.23 (t, 1H), 7.62 (d, 2H), 9.83 (s, 1H), 12.40 (s, 1H).

b) 4-[N-(1H-imidazol-1-yl)amino]benzonitrile

35% hydrogen peroxide (4.90 ml, 55.5 mmol) was added dropwise to an ice-cooled suspension of 4-[N-(2,3-dihydro-1H-imidazol-1-yl-2-thione)amino]benzonitrile (4.00 g, 18.50 mmol) in acetic acid (20 ml). When TLC showed complete reaction, the reaction mixture was diluted with water, adjusted to pH 11 with sodium hydroxide, treated with sodium hydrogen sulfite and extracted with ethyl acetate. The organic layer was dried over sodium sulfate and concentrated under vacuum. Flash chromatography on silica gel (toluene/dioxane: 6/4) yielded a pure oil and crystallization from ethanol afforded white crystals (4.40 g, 58%), mp: 162° C.

$^1$H-NMR (DMSOd$_6$): 6.50 (d, 2H), 7.08 (s, 1H), 7.30 (s, 1H), 7.66 (d, 2H), 7.83 (s, 1H).

Preparation of Benzothiophene Derivatives (14) and (20)

EXAMPLE 3

1-Chloro-3-(3-methoxyphenyl)sulfanyl-propan-2-one

To a stirred solution of 1,3-dichloro-2-propanone (12.70 g, 0.1 mol) in methanol/water (100 ml, 1:3) at 0° C. is added a suspension of 3-methoxybenzenethiol (14.02 g, 0.1 mol) and sodium hydroxide (4.00 g, 0.10 g) in water (100 ml). The mixture is stirred at 0° C. for 7 h and at mom temperature for 10 h. The precipitated product is extracted with dichloromethane (100 ml), washed with water (80 ml), and dried with sodium sulfate. After removal of the solvent, we obtained the good product (oil, 18.70 g).

$^1$H-NMR (CDCl$_3$): 3.80 (s, 3H), 3.83 (s, 2H), 4.29 (s, 2H), 6.78 (dd, 1H), 6.98 (d, 1H), 6.90 (dd, 1H), 7.21 (t, 1H).

EXAMPLE 4

3-Chloromethyl-6-methoxy-benzothiophene

A solution of the above thio compound (17.50 g, 75.85 mmol) in CH$_2$Cl$_2$ (1700 ml) was added dropwise to a solution of BF$_3$.Et$_2$O (10.60 ml, 83.44 mmol) in CH$_2$Cl$_2$ (100 ml) at room temperature under nitrogen atmosphere. The mixture was stirred overnight and after hydrolysis with aqueous NaHCO$_3$ solution, the reaction mixture was stirred until both phases became clear. The CH$_2$Cl$_2$ layer was separated, and the aqueous layer was extracted with CH$_2$Cl$_2$. The combined organic phases were dried over Na$_2$SO$_4$, filtered, and concentrated under vacuum to give an oil (18.00 g). Flash chromatography on silica gel (toluene/petroleum spirit 40-60° C.: 5/5) yielded a 1:10 mixture of 3-chloromethylmethoxy-benzothiophene: 3-chloromethyl-6-methoxy-benzothiophene as an oil (12.35 g, 58%).

Major isomer $^1$H-NMR (CDCl$_3$): 3.89 (s, 3H), 4.82 (s, 2H), 7.08 (dd, 1H), 7.30 (s, 1H), 7.35 (d, 1H), 7.78 (d, 1H).

EXAMPLE 5

3-Bromo-6-benzyloxy-benzothiophene

N-bromosuccinimide (15.70 g, 83.92 mmol) and p-toluenesulfonic add (2.70 g, 15.68 mmol) were added to a solution of 6-benzyloxy-benzothiophene (Zhengying C., CN 1370533 A, 21.2 g, 88.33 mmol) in 1,2-dichloroethane (120 ml). The mixture was maintained at 80° C. for 35 min, cooled in an ice bath, and the succinimide was removed by filtration. The solution was extracted with saturated sodium bicarbonate solution, dried over Na$_2$SO$_4$, filtered, and concentrated under vacuum to give an oil. Crystallisation from pentane afforded a white solid (21.60 g, 92%, mp: 68° C.).

$^1$H-NMR (DMSOd$_6$): 5.14 (s, 2H), 7.08 (dd, 1H), 7.25-7.55 (m, 6H), 7.65 (d, 1H), 7.76 (d, 1H).

EXAMPLE 6

3-Bromo-6-benzyloxy-benzothiophene-1,1-dioxyde

To a solution of 3-bromo-6-benzyloxy-benzothiophene (2.00 g, 6.27 mmol) in dichloromethane (50 ml) and trifluoroacetic acid (1.5 ml) was added 35% aqueous hydrogen peroxide (2.00 ml, 19.54 mmol). After 8 h at 50° C. the mixture was hydrolysed with saturated aqueous NaHCO$_3$, extracted with dichloromethane, dried over Na$_2$SO$_4$, filtered, and concentrated under vacuum to give the crude product. Flash chromatography on silica gel (toluene/ethyl acetate: 9/1) yielded a limpid oil (1.10 g, 55%).

$^1$H-NMR (DMSOd$_6$): 5.20 (s, 2H), 7.20-7.60 (m, 7H), 7.72 (d, 1H), 7.83 (s, 1H).

EXAMPLE 7

(6-Benzyloxy-benzothien-2-yl)methanol

To a solution of 6-benzyloxy-benzothiophene-2-carbaldehyde (described by Nomura Y., WO 9635688 A1, 6.50 g, 24.20 mmol) in THF (50 ml) was added dropwise to a −30° C. cooled suspension of LiAlH$_4$ (0.85 g, 22.26 mmol). After warming up to room temperature the mixture was stirred overnight, cooled to −10° C., hydrolyzed with ice water, extracted with dichloromethane, dried over Na$_2$SO$_4$, filtered and concentrated under vacuum to give the crude product. Flash chromatography on silica gel (toluene/ethyl acetate: 7/3) yielded a limpid oil (4.50 g, 69%).

¹H-NMR (DMSOd₆): 4.68 (s, 2H), 5.13 (s, 2H), 5.60 (s, 1H), 7.00 (dd, 1H), 7.14 (s, 1H), 7.25-7.80 (m, 7H).

EXAMPLE 8

6-Benzyloxy-2-(chloromethyl)-benzothiophene

Sulfonyl chloride (20 ml) is added to a solution of (6-benzyloxy-benzothien-2-yl) methanol (4.20 g, 15.50 mmol) in dichloromethane (40 ml). The mixture was maintained at reflux for 2 h, cooled at room temperature then concentrated under vacuum to give 4.20 g as an oil.
¹H-NMR (CDCl₃): 4.75 (s, 2H), 5.04 (s, 2H), 6.95 (dd, 1H), 7.10 (s, 1H), 7.20-7.60 (m, 7H).
Preparation of Imidazoles of Formula (8, 33, 35)
Using the same procedure as described in example 2, but replacing the 4-cyanophenylhydrazine, hydrochloride by:
N¹-(4-cyanophenylmethyl)-N'-(4-methoxyphenyl)hydrazine, the following compound was obtained:

EXAMPLE 9

4-[N-(1H-imidazol-1-yl)-N-(4-methoxyphenyl) amino]methylbenzonitrile

¹H-NMR (DMSO d₆): 3.70 (s, 3H), 4.90 (s, 2H), 6.60-7.00 (m, 5H), 7.40 (s, 1H), 7.55 (d, 2H), 7.70 (s, 1H), 7.78 (d, 2H).
Crystallization from hydrochloric ethanol yielded white crystals (5.70 g, 66%). mp: 207° C.
¹H-NMR (DMSO d₆): 3.70 (s, 3H), 4.97 (s, 2H), 6.93 (d, 2H), 7.13 (d, 2H), 7.45 (d, 2H), 7.70 (s, 1H), 7.84 (d, 2H), 8.04 (s, 1H), 8.18 (s, 1H), 9.55 (s, 1H).

EXAMPLE 10

4-[N-(4-hydroxyphenyl)-N-(1H-imidazol-1-yl) amino]methylbenzonitrile

A solution of boron tribromide (60 ml, 60.00 mmol) in 20 ml of dichloromethane is added to a cold (0-5° C.) solution of 4-[N-(1H-imidazol-1-yl)-N-(4 methoxyphenyl)amino]methylbenzonitrile (4.60 g, 15.11 mmol). After 1 h at room temperature the mixture was hydrolysed with saturated aqueous NaHCO₃, filtered, washed with water (50 ml) and with dichloromethane (20 ml) to give a brown solid (4.00 g). Crystallization from acetone yielded a brown solid (3.00 g, 68%) mp: 150° C.
¹H-NMR (DMSO d₆): 4.84 (s, 2H), 6.70 (s, 4H), 6.90 (s, 1H), 7.45-7.62 (m, 3H), 7.62-7.90 (m, 3H), 9.25 (s, 1H).

EXAMPLE 11

4-[N-(4-hydroxyphenylmethyl)-N-(1H-imidazol-1-yl)amino]benzonitrile 4-hydroxybenzylbromide (15.6 g, 84.3 mmol, prepared following Wissner A. et al., J. Med. Chem. 1992, 35, 1650) was added to a mixture of 4-[N-(1H-imidazol-1-yl)amino] benzonitrile (10.00 g, 54.30 mmol) and K₂CO₃ (8.20 g, 59.70 mmol) in dry THF (150 ml) at room temperature. The mixture was then stirred at room temperature for 2 h and after poured into water and extracted with ethyl acetate, dried over Na₂SO₄, filtered, and concentrated under vacuum to give the crude product (16.00 g as solid). Crystallization from ethyl acetate with ethanol yielded the expected product (6.50 g, 41%, mp: 180° C.)

¹H-NMR (DMSO d₆): 4.80 (s, 2H), 6.65 (d, 2H), 6.91 (s, 1H), 7.04 (d, 1H), 7.20 (s, 1H), 7.56 (s, 1H), 7.63 (d, 2H).
Using the same procedure but replacing the 4-hydroxybenzylbromide by:
3-chloro-4-hydroxybenzylbromide
3-bromo-4-hydroxybenzylbromide
4-hydroxy-3-methoxybenzylbromide
2,3,5,6-tetrafluoro-4-hydroxybenzylchloride (prepared following Angyal S. J. et al., J. Chem. Soc. 1950, 2141)
3-formyl-4-hydroxybenzylchloride (prepared following Angyal S. J. et al., J. Chem. Soc. 1950, 2141)
1-benzyloxy-4-(2-bromo-ethoxy)-benzene (prepared following Brinkman J. and al. Bioorg. Med. Chem. Lett., 1996, 6, 21, 2491-94)
2-chloro-5-chloromethyl-pyridine
4-(bromomethyl)benzene sulfonamide (prepared following Colescott R. and all. J. Am. Chem. Soc., 1957, 79, 4232-35)
4-(chloromethyl)-2-nitro-phenol (prepared following Bayer Patent: DE 132475)
5-chloromethyl-2-methoxy-benzoic add (prepared following Leonard F. and all. J. Med. Chem., 1965, 8, 812-15)
the following compounds were respectively obtained:

EXAMPLE 12

4-[N-(3-chloro-4-hydroxyphenylmethyl)-N-(1H-imidazol-1-yl)amino]benzonitrile mp 195° C.
¹H-NMR (DMSOd₆): 4.88 (s, 2H), 6.67 (d, 2H), 6.88 (d, 2H), 6.98 (s, 1H), 7.05 (dd, 1H), 7.24 (d, 1H), 7.33 (s, 1H), 7.70 (s, 1H), 7.72 (d, 2H), 10.28 (s, 1H).

EXAMPLE 13

4-[N-(3-bromo-4-hydroxyphenylmethyl)-N-(1H-imidazol-1-yl)amino]benzonitrile mp 198° C.
¹H-NMR (DMSOd₆): 4.90 (s, 2H), 6.65 (d, 2H), 6.85 (d, 1H), 6.99 (s, 1H), 7.07 (d, 1H), 7.30 (s, 1H), 7.40 (s, 1H), 7.65 (s, 1H), 7.67 (d, 2H), 10.40 (s, 1H).

EXAMPLE 14

4-[N-(4-hydroxy-3-methoxyphenylmethyl)-N-(1H-imidazol-1-yl)amino]benzonitrile mp 215° C.
¹H-NMR (DMSOd₆): 3.70 (s, 3H), 4.89 (s, 2H), 6.68 (s, 2H), 6.70 (d, 2H), 6.80 (s, 1H), 6.99 (s, 1H), 7.30 (s, 1H), 7.63 (s, 1H), 7.72 (d, 2H), 9.20 (s, 1H).

EXAMPLE 15

4-[N-(2,3,5,6-tetrafluoro-4-hydroxyphenylmethyl)-N-(1H-imidazol-1-yl)amino]benzonitrile mp 243° C.
¹H-NMR (DMSOd₆): 5.09 (s, 2H), 6.72 (d, 2H), 7.00 (s, 1H), 7.32 (s, 1H), 7.69 (d, 2H), 7.77 (s, 1H), 11.80 (s, 1H).

EXAMPLE 16

4-[N-(3-formyl-4-hydroxyphenylmethyl)-N-(1H-imidazol-1-yl)amino]benzonitrile mp 160° C.
¹H-NMR (DMSOd₆): 4.95 (s, 2H), 6.70 (d, 2H), 6.90 (s, 1H), 6.96 (d, 1H), 7.35 (s, 1H), 7.44 (dd, 1H), 7.58 (d, 1H), 7.67 (s, 1H), 7.71 (d, 2H), 10.20 (s, 1H), 10.75 (s, 1H).

EXAMPLE 17

4-{N-[2-(4-benzyloxy-phenoxy)ethyl]-N-(1H-imidazol-1-yl)amino]}benzonitrile $^1$H-NMR (DMSO d$_6$): 3.95-4.10 (m, 2H), 4.11-4.28 (m, 2H), 5.01 (s, 2H), 6.60 (d, 2H), 6.82 (d, 2H), 7.95 (d, 2H), 7.03-7.50 (m, 7H), 7.69 (d, 2H), 7.88 (s, 1H).

EXAMPLE 18

4-{N-[(6-chloropyridin-3-yl)methyl]-N-(1H-imidazol-1-yl)amino}benzonitrile mp 156° C.
$^1$H-NMR (DMSO d$_6$): 5.10 (s, 2H), 6.71 (d, 2H), 7.00 (s, 1H), 7.42 (s, 1H), 7.49 (d, 1H), 7.55-7.90 (m, 4H), 8.34 (d, 1H).

EXAMPLE 19

4-{[N-(4-cyanophenyl)-N-(1H-imidazol-1-yl)amino]methyl}benzene sulfonamide mp 150° C.
$^1$H-NMR (DMSO d$_6$): 5.15 (s, 2H), 6.62 (d, 2H), 7.00 (s, 1H), 7.36 (s, 2H), 7.45 (s, 1H), 7.55 (d, 2H), 7.65-7.90 (m, 5H).

EXAMPLE 20

4-[N-(4-hydroxy-3-nitrophenylmethyl)-N-(1H-imidazol-1-yl)amino]benzonitrile mp 205° C.
$^1$H-NMR (DMSO d$_6$): 4.98 (s, 2H), 6.72 (d, 2H), 7.00 (s, 1H), 7.06 (d, 1H), 7.39 (s, 1H), 7.48 (d, 1H), 7.60-7.78 (m, 3H), 7.82 (s, 1H).

EXAMPLE 21

5-{[N-(4-cyanophenyl)-N-(1H-imidazol-1-yl)amino]methyl}-2-methoxybenzoic acid mp 187° C.
$^1$H-NMR (DMSO d$_6$): 3.79 (s, 3H), 5.00 (s, 2H), 6.69 (d, 2H), 6.98 (s, 1H), 7.05 (d, 1H), 7.31 (s, 1H), 7.39 (dd, 1H), 7.55 (d, 1H), 7.62-7.85 (m, 3H).

EXAMPLE 22

4-[N-(1H-imidazol-1-yl)-N-(4-nitrophenyl)amino]benzonitrile

4[N-(1H-imidazol-1-yl)amino]benzonitrile (10.00 g, 54.30 mmol) was added portionwise to a suspension of potassium tert-butoxide (6.69 g, 59.73 mM) in DMSO (100 ml) at (10-15° C.) with stirring. The mixture was stirred for 30 mn at room temperature, and then 4-nitfluorobenzene (7.60 g, 54.00 mM) in DMSO (15 ml) was added dropwise while keeping the temperature below 30° C. After 2 h, the mixture was poured into water (800 ml) and the resulting precipitate was collected by filtration and purified by crystallization from ethanol (1.00 g, 48%, mp: 188° C.).
$^1$H-NMR (DMSOd$_6$): 7.00 (d, 2H), 7.17 (s, 1H), 7.26 (d, 2H), 7.65 (s, 1H), 7.90 (d, 2H), 8.20 (s, 1H), 7.22 (d, 2H).

Using the same procedure but replacing the 4-nitro-fluorobenzene by:
6-chloro-nicotinoyl chloride
4-fluorophenylacetyl chloride
4-hydroxyphenylacetyl chloride
4-hydroxyphenylpropanoyl chloride (prepared following Elias H. and all. Macromol. Chem. Phys., 1981, 182, 681-86)
4-phenylmethoxybenzene sulfonyl chloride (prepared following Toja E. and all. Eur. J. Med. Chem. 1991, 26, 403-13)
the following compounds were respectively obtained:

EXAMPLE 23

6-chloro-N-(4-cyanophenyl)-N-(1H-imidazol-1-yl)nicotinamide mp 132° C.
$^1$H-NMR (DMSO d$_6$): 6.98 (s, 1H), 7.40-7.62 (m, 3H), 7.70 (s, 1H), 7.95 (d, 2H), 8.00 (d, 1H), 8.19 (s, 1H), 8.57 (d, 1H).

EXAMPLE 24

N-(1H-imidazol-1-yl)-N-(4-cyanophenyl)-2-(4-fluorophenyl)acetamide mp 131° C.
$^1$H-NMR (DMSO d$_6$): 3.57 (s, 2H), 7.00-7.35 (m, 5H), 7.55 (d, 2H), 7.70 (s, 1H), 7.93 (d, 2H), 8.19 (s, 1H).

EXAMPLE 25

N-(1H-imidazol-1-yl)-N-(4-cyanophenyl)-2-(4-hydroxyphenyl)acetamide $^1$H-NMR (DMSO d$_6$): 3.32 (s, 2H), 6.65 (d, 2H), 6.87 (d, 2H), 7.08 (s, 1H), 7.50 (d, 2H), 7.70 (s, 1H), 7.90 (d, 2H), 8.10 (s, 1H), 9.30 (s, 1H).

EXAMPLE 26

N-(4-cyanophenyl)-3-(4-hydroxyphenyl)-N-(1H-imidazol-1-yl)propanamide mp 172° C.
$^1$H-NMR (DMSO d$_6$): 2.25-2.60 (m, 2H), 2.65-2.90 (m, 2H), 6.63 (d, 2H), 6.90 (d, 2H), 7.08 (s, 1H), 7.51 (d, 2H), 7.61 (s, 1H), 7.90 (d, 2H), 8.10 (s, 1H), 9.20 (s, 1H).

EXAMPLE 27

N-(4-cyanophenyl)-N-(1H-imidazol-1-yl)-4-(phenylmethoxy)-benzensulfonamide $^1$H-NMR (CDCl$_3$): 5.14 (s, 2H), 6.93 (t, 1H), 7.00-7.15 (m, 3H), 7.30-7.45 (m, 7H), 7.50 (s, 1H), 7.66 (d, 2H), 7.68 (d, 2H).

Preparation of Imidazoles of Formula (15), (21)

EXAMPLE 28

5-Nitro-[N-(4-cyanophenyl)-N-(1H-imidazol-1-yl)]-benzothiophene-2-carboxamide

5-Nitro-benzothiophene-2-carbonyl chloride (commercial compound, 10.00 g, 41.00 mmol) was added to a mixture of 4-[N-(1H-imidazol-1-yl)amino]benzonitrile (7.55 g, 41.00 mmol), TEA (20 ml, 143.00 mmol) in dry. THF (150 ml) at room temperature. The mixture was then stirred at room temperature overnight and the precipitate was filtrated, washed with THF, water to give the crude product as a solid (9.26 g). Crystallization with ethanol yielded white crystals (3.50 g, mp: 221° C.).
$^1$H-NMR (DMSO $d_6$): 7.10 (s, 1H), 7.54 (s, 1H), 7.70 (d, 2H), 7.82 (s, 1H), 7.98 (d, 2H), 8.15-8.40 (m, 3H), 8.89 (s, 1H).

Using the same procedure but replacing the 5-nitro-benzothiophene-2-carbonyl chloride by:
6-methoxy-benzothiophene-3-acetyl chloride (described by Sauter F., Monatshefte Fuer Chemie, 1968, 99, 2, 610-15) the following compound was obtained:

EXAMPLE 29

N-(4-cyanophenyl)-N-(1H-imidazol-1-yl)-2-(6-methoxy-benzothien-3-yl)acetamide mp: 104° C.
$^1$H-NMR (DMSO $d_6$): 3.75-3.85 (m, 5H), 7.02 (dd, 1H), 7.13 (s, 1H), 7.30 (s, 1H), 7.50-7.75 (m, 4H), 7.80 (s, 1H), 7.90 (d, 2H), 8.25 (s, 1H).

EXAMPLE 30

4-{N-[1H-imidazol-1-yl]-N-[(6-methoxy-benzothien-3-yl)methyl]amino}benzonitrile

3-Chloromethyl-6-methoxy-benzothiophene (12.35 g, 58.06 mmol) was added to a mixture of 4[N-(1H-imidazol-1-yl)amino]benzonitrile (9.72 g, 52.78 mmol), $K_2CO_3$ (14.60 g, 105.56 mmol) and potassium iodide (0.10 g, 0.60 mmol) in dry DMF (70 ml) at room temperature. The mixture was then stirred at room temperature overnight and after poured into water and extracted with ethyl acetate, dried over $Na_2SO_4$, filtered, and concentrated under vacuum to give the crude product as solid (14.30 g). Flash chromatography on silica gel (toluene/dioxan: 6/4) yielded the expected product (10.50 g, 55%, powder).
Crystallization with ethanol yielded white crystals (7.30 g, mp: 164° C.).
$^1$H-NMR (DMSO $d_6$): 3.80 (s, 3H), 5.25 (s, 2H), 6.74 (d, 2H), 6.93 (s, 1H), 7.02 (dd, 1H), 7.28 (s, 1H), 7.40 (s, 1H), 7.53 (s, 1H), 7.55 (s, 1H), 7.68 (d, 1H), 7.75 (d, 2H).

EXAMPLE 31

4-[N-(6-benzyloxy-1,1-dioxido-benzothien-3-yl)-N-(1H-imidazol-1-yl)amino]benzonitrile 4-[N-(1H-imidazol-1-yl)amino]benzonitrile (0.50 g, 27.14 mmol) was added portionwise to a suspension of potassium tert-butoxide (0.35 g, 31.00 mmol) in THF (20 ml) at (10-15° C.) with stirring. The mixture was stirred for 30 mn at room temperature, and then 3-bromo-6-benzyloxy-benzothiophene-1,1-dioxyde (1.10 g, 31.33 mM) in THF (5 ml) was added dropwise while keeping the temperature below 30° C. After one night, the mixture was poured into water (200 ml) and extracted with ethyl acetate, dried over $Na_2SO_4$, filtered, and concentrated under vacuum to give the crude product as an oil (2.50 g). Flash chromatography on silica gel (toluene/1,4-dioxan: 7/3) and crystallisation in ethanol yielded light brown crystals (1.20 g, 95%, mp: 146° C.).
$^1$H-NMR (DMSO $d_6$): 5.22 (s, 2H), 6.48 (s, 1H), 6.49 (d, 1H), 7.05-7.20 (m, 2H), 7.25-7.50 (m, 8H), 7.60 (d, 1H), 7.73 (s, 1H), 7.94 (d, 2H).

Using the same procedure but replacing the 3-bromo-6-benzyloxy-benzothiophene-1,1-dioxyde by:
6-benzyloxy-2-(chloromethyl)-benzothiophene
the following compound was obtained:

EXAMPLE 32

4-[N-[(6-benzyloxy-benzothien-2-yl)methyl]-N-(1H-imidazol-1-yl)amino]benzonitrile $^1$H-NMR (DMSO $d_6$): 5.12 (s, 2H), 5.30 (s, 2H), 6.72 (d, 2H), 7.00 (s, 1H), 7.04 (dd, 1H), 7.23 (s, 1H), 7.27-7.90 (m, 11H).

Preparation of Imidazoles of Formula (10), (16)

EXAMPLE 33

4-{N-[(6-hydroxy-benzothien-3-yl)methyl]-N-[1H-imidazol-1-yl-]amino}benzonitrile A solution of 4-{N-[1H-imidazol-1-yl]-N-[(6-methoxy-benzothien-3-yl)methyl]amino}benzonitrile (0.50 g, 1.39 mmol) in 10 ml of methylene chloride is added at room temperature to a solution 1M of boron tribromide in methylene chloride (1.50 ml, 1.52 mmol). After 2 h at room temperature the mixture was hydrolysed with saturated aqueous $NaHCO_3$, extracted with dichloromethane, dried over $Na_2SO_4$, filtered, and concentrated in vacuum. The crude product was purified by flash chromatography on silica gel (toluene/dioxan:6/4) to give the expected product (0.30 g, 62%, powder). Crystallization with ethanol yielded white crystalsl (0.10 g, mp: 169° C.).
$^1$H-NMR (DMSO $d_6$): 5.24 (s, 2H), 6.72 (d, 2H), 6.87 (dd, 1H), 6.94 (s, 1H), 7.27 (d, 2H), 7.29 (s, 1H), 7.55 (s, 1H), 7.56 (d, 1H), 7.75 (d, 2H), 9.67 (s, 1H).

Using the same procedure but replacing the 4-{N-[1H-imidazol-1-yl]-N-[(6-methoxy-benzothiophen-3-yl)methyl]amino}benzonitrile by:
N-(4-cyanophenyl)-N-(1H-imidazol-1-yl)-2-(6-methoxy-benzothien-3-yl)-acetamide, the following compound was obtained:

EXAMPLE 34

N-(4-cyanophenyl)-N-(1H-imidazol-1-yl)-2-(6-hydroxy-benzothien-3-yl)acetamide mp 179° C.
$^1$H-NMR (DMSO $d_6$): 3.72 (s, 2H), 6.85 (dd, 1H), 7.10 (d, 2H), 7.25 (d, 1H), 7.40-7.70 (m, 3H), 7.80 (s, 1H), 7.91 (d, 2H), 8.24 (s, 1H), 9.60 (s, 1H).

EXAMPLE 35

4-[N-(3-amino-4-hydroxy-phenylmethyl)-N-(1H-imidazol-1-yl)amino]benzonitrile

4-[N-(4-hydroxy-3-nitro-phenylmethyl)-N-(1H-imidazol-1-yl)amino]benzonitrile (2 g, 5.97 mmol) was hydrogenated over a suspension of Pd/C (10% Wt on carbon, 0.2 g) in ethanol (30 ml). When TLC showed complete reaction, the mixture was filtered on celatum, rinsed with EtOH. The solvent was concentrated under vacuum. Crystallisation from EtOH/petroleum ether yielded orange crystals (1.1 g, 60.5%, mp: 208° C.).

$^1$H-NMR (DMSO d$_6$): 4.60 (s, 2H), 4.79 (s, 2H), 6.80 (d, 1H), 6.40-6.80 (m, 4H), 6.99 (s, 1H), 7.25 (s, 1H), 7.50-7.80 (m, 3H), 9.07 (s, 1H).

Using the same procedure but replacing the 4-[N-(4-hydroxy-3-nitro-benzyl)-N-(1H-imidazol-1-yl)amino]benzonitrile by:
4{N-[2-(4-benzyloxy-phenoxy)ethyl]-N-(1H-imidazol-1-yl)amino]}-benzonitrile
N-(4-cyanophenyl)-N-(1H-imidazol-1-yl)-4-(phenyl-methoxy)-benzensulfonamide
the following compounds were respectively obtained:

EXAMPLE 36

4-{N-[2-(4-hydroxyphenoxy)ethyl]-N-(1H-imidazol-1-yl)amino}benzonitrile mp 188° C.
$^1$H-NMR (DMSO d$_6$): 4.99 (t, 2H), 4.17 (t, 2H), 6.40-6.85 (m, 6H), 7.10 (s, 1H), 7.40 (s, 1H), 7.68 (d, 2H), 7.86 (s, 1H), 8.95 (s, 1H).

EXAMPLE 37

N-(4-cyanophenyl)-N-(1H-imidazol-1-yl)-4-hydroxybenzensulfonamide mp 248° C.
$^1$H-NMR (DMSO d$_6$): 6.95 (d, 2H), 7.00 (s, 1H), 7.24 (s, 1H), 7.49 (d, 2H), 7.52 (d, 2H), 7.88 (s, 1H), 7.92 (d, 2H), 10.95 (s, 1H).

EXAMPLE 38

4-[N-[(6-hydroxy-1,1-dioxido-benzothien-3-yl)]-N-(1H-imidazol-1-yl)amino]benzonitrile A mixture of 4[N-[(6-benzyloxy-1,1-dioxido-benzothien-3-yl)]-N-(1H-imidazol-1-yl)amino]benzonitrile (3.00 g, 6.78 mmol), 10% Pd/C (0.50 g), THF (30 ml) and solution of ammonium formate (25% in H$_2$O, 30 ml) was stirred at ambient temperature for 6 h and filtered. The mixture was poured into water and extracted with ethyl acetate, dried over Na$_2$SO$_4$, filtered, and concentrated under vacuum to give the crude product (2.50 g as solid). Crystallisation from ethanol afforded white crystals (0.80 g, 26%, mp: 260° C.).

$^1$H-NMR (DMSO d$_6$): 6.25 (s, 1H), 6.29 (d, 1H), 6.82 (dd, 1H), 7.10 (s, 1H), 7.15 (s, 1H), 7.30 (d, 2H), 7.70 (s, 1H), 7.91 (d, 2H), 8.25 (s, 1H).

Using the same procedure but replacing the 4[N-[(6-benzyloxy-1,1-dioxido-benzothien-3-yl)]-N-(1H-imidazol-1-yl)amino]benzonitrile by:
4[N-[(6-benzyloxy-benzothien-2-yl)methyl]-N-(1H-imidazol-1-yl)amino]benzonitrile
the following compound was obtained:

EXAMPLE 39

4-[N-[(6-hydroxy-benzothien-2-yl)methyl]-N-(1H-imidazol-1-yl)amino]benzonitrile mp 230° C.
$^1$H-NMR (DMSO d$_6$): 5.28 (s, 2H), 6.70 (d, 2H), 6.82 (dd, 1H), 7.00 (s, 1H), 7.15-7.21 (m, 2H), 7.31 (s, 1H), 7.55 (d, 1H), 7.69-7.80 (m, 3H), 9.63 (s, 1H).

Preparation of Imidazoles of Formula (12), (18)

EXAMPLE 40

4-[N-(4-aminophenyl)-N-(1H-imidazol-1-yl)amino]benzonitrile

Hydrazine (1.52 ml, 49.00 mmol) was added portionwise to a suspension of 4-[N-(1H-imidazol-1-yl)-N-(4-nitrophenyl)amino]benzonitrile (3.00 g, 9.80 mM) and ruthenium, 5 wt. % on carbon (0.30 g, 0.15 mM) in ethanol (35 ml) at reflux with stirring. When TLC showed complete reaction, the mixture was cooled and the catalyst was filtered. The solvent was concentrated under vacuum. The residue was poured into water and extracted with dichloromethane, dried over Na$_2$SO$_4$, filtered, and concentrated under vacuum to give the crude product (2.50 g as solid). Crystallization from ethyl acetate with ethanol yielded the expected product (1.30 g, 50%, mp: 147° C.).

$^1$H-NMR (DMSOd$_6$): 5.50 (s, 2H), 6.30 (d, 2H), 6.69 (d, 2H), 7.09 (s, 1H), 7.29 (d, 2H), 7.63 (s, 1H), 7.65 (d, 2H), 8.14 (s, 1H).

EXAMPLE 41

5-Amino-[N-(4-cyanophenyl)-N-(1H-imidazol-1-yl)]-benzothiophene-2-carboxamide

Stannous chloride dihydrate (13.10 g, 58.00 mmol) was added portionwise to a stirred solution of 5-nitro-[N-(4-cyanophenyl)-N-(1H-imidazol-1-yl)]-benzothiophene-2-carboxamide (4.50 g, 11.6 mM) in ethanol (100 ml). The mixture was heated under reflux. When TLC showed complete reaction, the mixture was cooled and basified with saturated bicarbonate solution. The mixture was extracted with ethyl acetate, dried over Na$_2$SO$_4$, filtered, and concentrated under vacuum to give the crude product as a solid (3.90 g). Crystallization from methanol yielded the expected product (2.60 g, 63%, mp: 214° C.).

$^1$H-NMR (DMSOd$_6$): 6.70-6.98 (m, 3H), 7.07 (s, 1H), 7.40-7.25 (m, 4H), 7.26-7.96 (m, 3H).

General Procedure of Sulfamoylation
Preparation of Sulfamates (11, 17, 23) and Aminosulfonylamines (13, 19, 25)

EXAMPLE 42

Sulfamic add 4-[N-(4-cyanophenylmethyl)-N-(1H-imidazol-1yl)amino]phenyl ester

Sulfamoyl chloride (2.39 g, 20.69 mmol) was added to a solution of 4[N-(4-hydroxyphenyl)-N-(1H-imidazol-1-yl)amino]methylbenzonitrile (1.00 g, 3.45 mmol) in dry DMAc (36 ml) with ice cooling. The mixture was then stirred at room temperature for 6 h. After addition of TEA (3.40 ml, 24.73 ml), the mixture was poured into cold brine and extracted with ethyl acetate, dried over Na$_2$SO$_4$, filtered, and concentrated under vacuum to give the crude product (0.70 g as solid).

Crystallization from ethyl acetate yielded the expected product (0.40 g, 31%, mp: 60° C.).

$^1$H-NMR (DMSO d$_6$): 5.00 (s, 2H), 6.70 (d, 2H), 6.92 (s, 1H), 7.19 (d, 2H), 7.40 (s, 1H), 7.55 (d, 2H), 7.74 (s, 1H), 7.77 (d, 2H), 7.91 (s, 2H).

Using the same procedure but replacing the 4[N-(4-hydroxyphenyl)-N-(1H-imidazol-1-yl)amino]methylbenzonitrile by:

4-[N-(4-hydroxyphenylmethyl)-N-(1H-imidazol-1-yl)amino]benzonitrile
4[N-(3-chloro-4-hydroxyphenylmethyl)-N-(1H-imidazol-1-yl)amino]benzonitrile
4[N-(3-bromo-hydroxyphenylmethyl)-N-(1H-imidazol-1-yl)amino]benzonitrile
4[N-(3-methoxy-4-hydroxyphenylmethyl)-N-(1H-imidazol-1-yl)amino]benzonitrile
4-[N-(2,3,5,6-tetrafluoro-hydroxyphenylmethyl)-N-(1H-imidazol-1-yl)amino]benzonitrile
4[N-(3-formyl-+hydroxyphenylmethyl)-N-(1H-imidazol-1-yl)amino]benzonitrile
4[N-(4-aminophenyl)-N-(1H-imidazol-1-yl)amino]benzonitrile
N-(4-cyanophenyl)-N-(1H-imidazol-1-yl)-4-hydroxybenzensulfonamide
4-{N-[2-(4-hydroxyphenoxy)ethyl]-N-(1H-imidazol-1-yl)amino}benzonitrile
N-(1H-imidazol-1-yl)-N-(4-cyanophenyl)-2-(4-hydroxyphenyl)acetamide
N-(4-cyanophenyl)-3-(4-hydroxyphenyl)-N-(1H-imidazol-1-yl)propanamide
4[N-(3-amino-hydroxyphenylmethyl)-N-(1H-imidazol-1-yl)amino]benzonitrile
5-Amino[N-(4-cyanophenyl)-N-(1H-imidazol-1-yl)]-benzothiophene-2-carboxamide
4-[N-[(6-hydroxy-1,1-dioxido-benzothien-3-yl)]-N-(1H-imidazol-1-yl)amino]benzonitrile
N-(4-cyanophenyl)-N-(1H-imidazol-1-yl)-2-[(6-hydroxy-benzothien-2-yl)]acetamide
4-{N-[(6-hydroxy-benzothien-3-yl)]methyl]-N-[1H-imidazol-1-yl-]amino}benzonitrile
4-{N-[(6-hydroxy-benzothien-2-yl)methyl]-N-[1H-imidazol-1-yl-]amino}benzonitrile the following compounds were respectively obtained:

EXAMPLE 43

Sulfamic acid-4-{[N-(4-cyanophenyl)-N-(1H-imidazol-1yl)amino]methyl}phenyl ester mp 172° C.

$^1$H-NMR (DMSOd$_6$): 5.00 (s, 2H), 6.65 (d, 2H), 7.00 (s, 1H), 7.22 (d, 2H), 7.40 (s, 1H), 7.42 (d, 2H), 7.70 (s, 1H), 7.75 (d, 2H), 8.00 (s, 2H).

EXAMPLE 44

Sulfamic acid 2-chloro-4-{[N-(4-cyanophenyl)-N-(1H-imidazol-1yl)amino]methyl}phenyl ester $^1$H-NMR (DMSOd$_6$): 5.05 (s, 2H), 6.63 (d, 2H), 7.00 (s, 1H), 7.35-7.45 (m, 3H), 7.54 (s, 1H), 7.70 (d, 2H), 7.80 (s, 1H), 8.29 (s, 2H).

EXAMPLE 45

Sulfamic acid 2-bromo-4-{[N-(4-cyanophenyl)-N-(1H-imidazol-1yl)amino]methyl}phenyl ester, hydrochloride Crystallisation was performed in EtOH/HCl (mp 145° C.)
$^1$H-NMR (DMSOd$_6$): 5.15 (s, 2H), 6.90 (d, 2H), 7.48 (s, 2H), 7.60-7.85 (s, 5H), 8.08 (s, 1H), 8.32 (s, 2H), 9.51 (s, 1H).

EXAMPLE 46

Sulfamic acid 2-methoxy-4-{[N-(4-cyanophenyl)-N-(1H-imidazol-1yl)amino]methyl}phenyl ester mp 211° C.

$^1$H-NMR (DMSOd$_6$): 3.77 (s, 3H), 5.02 (s, 2H), 6.75 (d, 2H), 6.92 (d, 1H), 7.05 (s, 2H), 7.25 (d, 1H), 7.45 (s, 1H), 7.71 (d, 2H), 7.80 (s, 1H), 7.93 (s, 2H).

EXAMPLE 47

Sulfamic acid 2,3,5,6-tetrafluoro-4-{[N-(4-cyanophenyl)-N-(1H-imidazol-1yl)amino]methyl}phenyl ester $^1$H-NMR (DMSOd$_6$): 5.37 (s, 2H), 5.83 (s, 2H), 6.86 (d, 2H), 7.08 (s, 1H), 7.41 (s, 1H), 7.79 (s, 1H), 7.81 (d, 2H).

EXAMPLE 48

4-[N-[(2,2-dioxido-1,2,3-benzoxathiazin-6-yl)methyl]-N-(1H-imidazol-1-yl)amino]benzonitrile mp 180° C.

$^1$H-NMR (DMSOd$_6$): 5.17 (s, 2H), 6.67 (d, 2H), 7.02 (s, 1H), 7.46 (s, 1H), 7.50 (d, 2H), 7.74 (d, 2H), 7.82 (dd, 1H), 7.87 (s, 1H), 8.02 (d, 1H), 9.19 (s, 1H).

EXAMPLE 49

N-{4-[N-(4-cyanophenyl)-N-(1H-imidazol-1-yl)amino]phenyl}sulfamide mp 121° C.

$^1$H-NMR (DMSOd$_6$): 6.38 (d, 2H), 7.09 (s, 1H), 7.20 (s, 1H), 7.22 (d, 2H), 7.51 (d, 2H), 7.63 (s, 1H), 7.69 (d, 2H), 8.19 (s, 1H)

EXAMPLE 50

Sulfamic acid 4-{[N-(4-cyanophenyl)-N-(1H-imidazol-1yl)amino]sulfonylphenyl ester, hydrochloride Crystallisation was performed in EtOH/HCl
mp 200° C.

$^1$H-NMR (DMSOd$_6$): 7.57 (d, 2H), 7.60 (s, 1H), 7.70 (d, 2H), 7.80-8.10 (m, 5H), 8.40 (s, 2H), 9.30 (s, 1H).

EXAMPLE 51

Sulfamic acid 4-{2-[N-(4-cyanophenyl)-N-(1H-imidazol-1yl)amino]ethoxy}phenyl ester mp 174° C.

$^1$H-NMR (DMSOd$_6$): 4.08 (t, 2H), 4.23 (t, 2H), 6.60 (d, 2H), 6.95 (d, 2H), 7.10 (s, 1H), 7.18 (d, 2H), 7.42 (s, 1H), 7.70 (d, 2H), 7.88 (s, 3H).

EXAMPLE 52

Sulfamic add 4-{[N-(4-cyanophenyl)-N-(1H-imidazol-1yl)-carbamoyl]-methyl}phenyl ester $^1$H-NMR (DMSOd$_6$): 3.32 (s, 2H), 7.12 (s, 1H), 7.18-7.32 (m, 4H), 7.50-7.60 (d, 2H), 7.71 (s, 1H), 7.85-8.05 (m, 4H), 8.20 (s, 1H).

EXAMPLE 53

Sulfamic acid 4-[N-(4-cyanophenyl)-N-(1H-imidazol-1yl)amino]-3-oxopropyl}phenyl ester mp 100° C.
$^1$H-NMR (DMSOd$_6$): 2.45 (t, 2H), 3.85 (t, 2H), 7.10 (s, 1H); 7.12-7.30 (m, 4H), 7.55 (d, 2H), 7.65 (s, 1H), 7.90 (m, 4H), 8.12 (s, 1H).

EXAMPLE 54

Sulfamic acid 3-(aminosulfonyl)amino-4-{[N-(4-cyanophenyl)-N-(1H-imidazol-1yl)amino]methyl}phenyl ester mp 197° C.
$^1$H-NMR (DMSOd$_6$): 5.00 (s, 2H), 6.71 (d, 2H), 6.93 (d, 1H), 7.02 (s, 2H), 7.21 (d, 1H), 7.48 (s, 1H), 7.61 (d, 2H), 7.74 (s, 1H), 7.92 (s, 2H), 8.10 (s, 2H).

EXAMPLE 55

5-(Aminosulfonyl)amino-[N-(4-cyanophenyl)-N-(1H-imidazol-1-yl)]-benzothiophene-2-carboxamide mp: 169° C.
$^1$H-NMR (DMSO d$_6$): 6.87 (d, 1H), 7.05-7.30 (m, 4H), 7.56 (s, 1H), 7.67 (d, 2H), 7.80-8.10 (m, 4H), 7.86 (s, 1H), 9.65 (s, 1H).

EXAMPLE 56

Sulfamic acid 3-[N-(4-cyanophenyl)-N-(1H-imidazol-1yl)amino]-1,1-dioxido-benzothien-6-yl ester mp 172° C.
$^1$H-NMR (DMSO d$_6$): 6.24 (s, 1H), 6.29 (d, 1H), 6.85 (dd, 1H), 7.15 (s, 1H), 7.20 (s, 1H), 7.30 (d, 2H), 7.65 (s, 1H), 7.95 (d, 2H), 8.05 (s, 2H), 8.25 (s, 1H).

EXAMPLE 57

Sulfamic acid 3-{2-[N-(4-cyanophenyl)-N-(1H-imidazol-1yl)amino]-2-oxoethyl}-benzothien-6-yl ester $^1$H-NMR (DMSO d$_6$): 3.84 (s, 2H), 7.15 (s, 1H), 7.28-7.37 (dd, 1H), 7.51-7.65 (m, 3H), 7.80-7.98 (m, 5H), 8.01 (s, 2H), 8.29 (s, 1H).

EXAMPLE 58

Sulfamic acid 3-{[N-(4-cyanophenyl)-N-(1H-imidazol-1yl)amino]methyl}-benzothien-6-yl ester mp 193° C.
$^1$H-NMR (DMSO d$_6$): 5.30 (s, 2H), 6.80 (d, 2H), 6.97 (s, 1H), 7.30-7.40 (m, 2H), 7.56 (s, 1H), 7.68 (s, 1H), 7.75 (d, 2H), 7.80-7.95 (m, 2H), 8.05 (s, 2H).

EXAMPLE 59

Sulfamic acid 2-{[N-(4-cyanophenyl)-N-(1H-imidazol-1yl)amino]methyl}-benzothien-6-yl ester mp 178° C.
$^1$H-NMR (DMSO dr): 5.17 (s, 2H), 6.65 (d, 2H), 6.89 (dd, 1H), 6.94 (s, 1H), 7.20 (d, 2H), 7.27 (s, 1H), 7.45 (s, 1H), 7.58 (d, 1H), 7.72 (d, 2H), 8.00 (s, 2H).

Using the same procedure as example 13 but replacing the 4-[N-(4-hydroxyphenyl)-N-(1H-imidazol-1-yl)amino]methylbenzonitrile by:
4[N-(3-bromo-hydroxyphenylmethyl)-N-(1H-imidazol-1-yl)amino]benzonitrile The following compounds was obtained as a by-product:

EXAMPLE 60

2-Bromo-4-{[N-(4-cyanophenyl)-N-(1H-imidazol-1yl)amino]methyl}phenyl amidimidodisulfate acid mp 220° C.
$^1$H-NMR (DMSOd$_6$): 5.00 (s, 2H), 5.70 (s, 2H), 6.65 (d, 2H), 7.03 (s, 1H), 7.42 (dd, 1H), 7.50 (s, 1H), 7.55 (d, 1H), 7.65 (d, 1H), 7.72 (d, 2H), 7.81 (s, 1H).

Preparation of Other Compounds (8)

EXAMPLE 61

4-[N-[(2,2-dioxido-3,4-dihydro-1,2,3-benzoxathiazin-6-yl)methyl]-N-(1H-imidazol-1-yl)amino]benzonitrile To a suspension of +[N-[(2,2-dioxido-1,2,3-benzoxathiazin-6-yl)methyl]-N-(1H-imidazol-1-yl)amino]benzonitrile (0.40 g, 1.05 mmol) in methanol (8 ml) was added portionwise NaBH$_4$ (0.08 g, 2.11 mmol) and the reaction mixture was stirred at room temperature for 3 h. After addition of a saturated solution of NH$_4$Cl (3 ml) and water (40 ml), the precipitate obtained was filtered, washed with water and dried to give a white solid. Crystallization from ethyl acetate with ethanol yielded the expected product (0.40 g, 82%, mp: 190° C.).

$^1$H-NMR (DMSOd$_6$): 4.55 (d, 2H), 5.04 (s, 2H), 6.64 (d, 2H), 7.02 (s, 1H), 7.03 (d, 1H), 7.27 (d, 1H), 7.30 (s, 1H), 7.41 (s, 1H), 7.70 (d, 2H), 7.85 (s, 1H), 8.56 (t, 1H).

EXAMPLE 62

5-{[N-(4-cyanophenyl)-N-(1H-imidazol-1-yl)amino]methyl}-2-hydroxybenzoic acid

A mixture of 5-{[N-(+cyanophenyl)-N-(1H-imidazol-1-yl)amino]methyl}-2-methoxybenzoic add (1.00 g, 2.85 mmol) and piperidine (0.42 ml, 8.57 mmol) in dimethylacetamide (DMA) (2 ml) was heated at 150° C. When starting material had disappeared (TLC monitoring), the solvent was removed in vacuo. Flash chromatography on silica gel (MeOH/dichloromethane:5/95) and crystallization from ethanol afforded white crystals (53 mg, 6%, mp: 260° C.).

$^1$H-NMR (DMSO d$_6$): 4.85 (s, 2H), 6.54 (d, 1H), 6.66 (d, 2H), 6.95 (s, 1H), 7.05 (dd, 1H), 7.24 (s, 1H), 7.50-7.60 (m, 2H), 7.68 (d, 2H).

EXAMPLE 63

4-[N-(1H-imidazol-1-yl)-N-(phenyl)amino]benzonitrile

4[N-(1H-imidazol-1-yl)-N-(+nitrophenyl)amino]benzonitrile (3.91 g, 12.80 mmol) was placed in a hydrogenation flask and dissolved in acetic anhydride (60 ml) and acetic acid (60 ml). Palladium 10% on C, 0.20 g) was added, and the bottle was attached to a Parr hydrogenation apparatus. Hydrogenation was carried out with shaking for 3 h at 25 psi H$_2$. The catalyst was removed by filtration and the solution was cooled in a bath for 30 mn. Sodium nitrite (0.97 g, 14.00 mmol) was added to the mixture, and the vessels are lightly capped. The flask is kept in the ice bath for 2 h and allowed to warm to room temperature overnight. The mixture was poured into ice/water and the solid was filtered, washed with water (50 ml) to give crude product. Flash chromatography (toluen/dioxan:6/4) and crystallization from ethyl acetate with ethanol yielded the expected product (0.40 g, 8%, mp: 162° C.).

$^1$H-NMR (DMSO 6): 6.60 (d, 2H), 7.00-7.50 (m, 9H), 7.69 (s, 1H).

Preparation of Benzoxathiazole (8)

EXAMPLE 64

4-[N-(3-tosylamino-4-hydroxy-benzyl)-N-(1H-imidazol-1-yl)amino]benzonitrile

Tosyl chloride (3.5 g, 18.59 mmol) in CH$_2$Cl$_2$ (20 ml) was added dropwise to a solution of (1×1840) (5.4 g, 17.7 mmol) and pyridine (19.47 mmol, 1.6 ml) in CH$_2$Cl$_2$ (50 ml) at 0° C.

The mixture was then stirred at room temperature for 4 h then poured into water and extracted with EtOAc, dried over Na$_2$SO$_4$, filtered and concentrated under vacuum to give the crude product (8.1 g as orange solid).

Flash chromatography on silica gel (toluene dioxane 7/3) yielded yellow solid.

$^1$H-NMR (DMSO d$_6$): 2.32 (s, 3H), 4.85 (s, 2H), 6.60 (d, 2H), 6.62 (s, 1H), 6.80 (dd, 1H), 6.97 (s, 1H), 7.10-7.30 (m, 5H), 7.00 (d, 2H), 7.03 (s, 1H), 7.52 (d, 2H), 9.45 (s, 2H).

EXAMPLE 65

4-[N-[(2,2-dioxido-3-tosyl-3H-1,2,3-benzoxathiazol-5-yl)methyl]-N-(1H-imidazol-1-yl)amino]benzonitrile Sulfuryl chloride (0.60 ml, 7.40 mmol) in dichloromethane (50 ml) was added dropwise with stirring over a 30 mn period to 4[N-(3-tosylaminohydroxybenzyl)-N-(1H-imidazol-1-yl)amino]benzonitrile (3.40 g, 7.40 mmol) and triethylamine (2.10 ml, 14.81 mmol) in dichloromethane (6 ml) at −78° C. After an additional 15 mn, the mixture was allowed to room temperature for 4 h. The reaction mixture was diluted with water, extracted with dichloromethane. The organic layer was dried over sodium sulfate and concentrated under vacuum.

Flash chromatography on silica gel (toluene/dioxane:5/5) yielded a pure oil (1.60 g, 41%).

$^1$H-NMR (DMSO d$_6$): 2.39 (s, 3H), 5.18 (s, 2H), 6.80 (d, 2H), 7.00-7.50 (m, 6H), 7.60-7.85 (m, 5H), 8.02 (s, 1H).

EXAMPLE 66

4-[N-[(2,2-dioxido-3H-1,2,3-benzoxathiazol-5-yl)methyl]-N-(1H-imidazol-1-yl)amino]benzonitrile Potassium fluoride (0.36 g, 6.14 mmol) in water (5 ml) was added to 4[N-[(2,2-dioxido-3-tosyl-3H-1,2,3-benzoxathiazol-5-yl)methyl]-N-(1H-imidazol-1-yl)amino]benzonitrile (1.60 g, 3.07 mmol) in acetonitrile (15 ml) at room temperature. The solution was stirred overnight, concentrated, extracted with dichloromethane. The organic layer was dried over sodium sulfate and concentrated under vacuum. Flash chromatography on silica gel (toluene/dioxane: 5/5) yielded an oil and crystallization from ethanol yielded the expected product (0.17 g, 15%, mp: 230° C.).

$^1$H-NMR (DMSO d$_6$): 4.84 (s, 2H), 6.38 (dd, 1H), 6.42 (d, 1H), 6.63 (d, 1H), 6.69 (d, 2H), 7.15 (s, 1H), 7.43 (s, 1H), 7.70 (d, 2H), 8.02 (s, 1H).

Preparation of Phenyl Ureas (27)

EXAMPLE 67

N-(4-cyanopheny)-N-(1H-imidazol-1-yl)-N'-phenylurea

Phenyl isocyanate (3.6 ml, 32.6 mmol) was added to a solution of 4-[N-(1H-imidazol-1-yl)amino]benzonitrile (5 g, 27.17 mmol) in THF (50 ml). The mixture was stirred at 50° C. overnight and after evaporation was crystallised in acetone/EtOH to give white crystals (2.5 g, 30.3%, 178° C.).

$^1$H-NMR (DMSO d$_6$): 6.59 (s, 1H), 7.05-7.40 (m, 9H), 7.52 (d, 2H), 7.83 (s, 1H).

Biological Test Results

Inhibition of Steroid Sulfatase, Aromatase and Carbonic Anhydrase II In Vitro

Estrone sulfate (E$_1$S) is a major circulating plasma estrogen that is converted by the steroid sulfatase enzyme into estrone (E$_1$), which in turn can be transformed into estradiol (E$_2$) by enzymatic reduction.

The inhibition of E$_2$ synthesis by aromatase inhibitors has been clinically proved to be a good way to halt the progress of hormone-dependent breast tumors. More recently, the inhibition of the steroid sulfatase pathway emerged as an alternative. Therefore, the development of compounds able to inhibit both aromatase and steroid sulfatase inhibition appears as a new and suitable approach to inhibit tumor growth.

Human carbonic anhydrases catalyses the conversion between carbon dioxide (CO$_2$) and the bicarbonate ion (HCO$_3^-$), and are involved in numerous physiological and pathological processes. They include hormone-dependent and non-hormone-dependent cancerogenesis, metastasis process and hypoxic tumors that are less responsive to classical chemo/radio-therapy. The inhibition of human carbonic anhydrases could be therefore a valuable additional activity for dual aromatase and sulfatase inhibitor (DASI) compounds. In particular, EMATE was found to have a human carbonic anhydrases inhibitory potency similar to that of acetazolamide, a well-known sulfonamide human carbonic anhydrases inhibitor. The aim of these experiments was to evaluate in vitro the inhibitory potential of new compounds on aromatase and/or steroid sulfatase activity. In addition, inhibition on human carbonic anhydrase II activity (as an example of human carbonic anhydrase) for some of them were evaluated in comparison with 6,6,7 COUMATE and acetazolamide.

Materials & Methods a) Aromatase Activity

The JEG-3 cell line, derived from a human placental choriocarcinoma, constitutively overexpresses human aromatase and represents a relevant model for assaying putative aromatase inhibitors in vitro. Aromatase activity was determined by the tritiated water method. In brief, cells were first seeded into 96-well microplates in decomplemented fetal calf serum (dFCS) supplemented medium. 24 hours later, cells were rinsed and fresh medium containing $1\beta$-$^3$H-androstenedione as aromatase substrate was added together with test compounds at concentrations ranging from $10^{-12}$ M to $10^{-5}$ M. After 2 hours of incubation, a fraction of the medium was transferred to homologous new 96-well microplates and a dextran-coated charcoal solution was added to each well. Following standing on ice for 10 minutes, microplates were centrifuged (1500 g; 4° C.). All steroids, including the radioactive substrate and the newly biosynthesized estrogens, were adsorbed on charcoal; only $^3$H-water specifically formed during aromatisation of $1\beta$-$^3$H-androstenedione, remained in the supernatant. The radioactivity in the supernatant was measured by liquid scintillation counting. In parallel, cell solubilization was performed in ethylenediamine tetraacetate solution. DNA content was measured by a standard fluorimetric method using the Hoechst 33258 fluorochrome. Finally, aromatase activity was expressed in fmoles of $^3$H-water formed/2 hours/µg DNA and aromatase inhibition as a percentage of control activity without inhibitor. A non-linear fit analysis (GraphPad Prism Software) of % of inhibition vs. inhibitor concentration allowed the determination of the 50% inhibitory concentration ($IC_{50}$): the lowest $IC_{50}$s correspond to the most potent inhibitors (Table 1).

b) Steroid Sulfatase Activity

The JEG-3 cell line is intrinsically very rich in human estrone sulfatase and therefore is a useful biological system to evaluate new steroid sulfatase inhibitors in vitro. Assays were carried out with cells in logarithmic growth phase on 96-well microplates. 24 h before studies, cells were seeded in decomplemented fetal calf serum (dFCS) supplemented medium. The medium was removed 24 h later and cells were rinsed with PBS to eliminate any trace of dFCS. Then, $^3$H-$E_1$S was added in dFCS free medium, followed by test compounds at concentrations ranging from $10^{-12}$ M to $10^{-5}$ M. After 4 h of treatment, the medium was transferred into 96-deep-well microplates and centrifuged at 200×g for 10 min to pellet cells before toluene extraction. A fraction of the medium was used for toluene extraction in order to separate the conjugated substrate from non-conjugated products. The radioactivity in the toluene phase was measured by liquid scintillation counting. In parallel, after cell solubilization in a ethylenediamine tetraacetate solution, DNA content was measured by a standard fluorimetric method using the Hoechst 33258 fluorochrome. Finally, estrone sulfatase activity was expressed in pmoles of $^3$H-$E_1$+$^3$H-$E_2$ formed/4 hours/mg DNA and estrone sulfatase inhibition as a percentage of control activity without inhibitor. A non linear fit analysis (GraphPad Prism Software) of % inhibition vs. inhibitor concentration allowed the determination of the 50% inhibitory concentration ($IC_{50}$): the lowest $IC_{50}$s correspond to the most potent inhibitors (Table 1).

c) Dual Aromatase and Steroid Sulfatase Activities

In order to evaluate the inhibitory potency of DASI compounds in parallel on both human aromatase and steroid sulfatase activities, a new in vitro model was set up using JEG-3 cells. The experimental conditions of the steroid sulfatase model previously described was adopted with slight modifications: the presence of the two substrates $^3$-$HE_1$S and $1\beta$-$^3$H-androstenedione into the medium and an incubation period of 2 hours. Results were expressed in pmoles of product formed ($^3$H-$E_1$+$^3$H-$E_2$ or $^3$H$_2$O)/2 hours/mg DNA (Table 1).

d) Alkaline Phosphatase Activity

Ishikawa cells were plated into 96-well microplates 48 hours before studies. The next day, the medium was replaced by phenol red free medium supplemented with 5% charcoal-stripped dFCS. 24 hours later, the medium was renewed and compounds were added to the plated cells and incubated for an additional four-day period. For each compound, the tested concentrations ranged from $10^{-12}$ M to $10^{-5}$ M, and the final vehicle concentration did not exceed 0.1%. At the end of the incubation period, alkaline phosphatase activity (APase) was assayed by a method involving the hydrolysis of p-nitrophenyl phosphate to p-nitrophenol and spectrophotometric determination of the product at 405 nm.

In brief, the microplates were first rinsed twice with cold phosphate buffered solution and then placed at −80° C. for at least 15 minutes. After thawing at room temperature, 50 µl ice-cold solution containing 5 mM p-nitrophenyl phosphate was added to each well. After a 15 to 60 minute incubation period at room temperature, the intensity of the yellow color generated by the production of p-nitrophenol was measured into each well at 405 nm.

For each tested concentration, APase activity, reflected by absorbance, was first expressed as fold increase over control (FI) and then as percentage of $E_2$ activity (10-8 M) chosen equal to 100%. Sigmoidal dose-response curves were plotted (GraphPad Prism Software) and 50% effective concentrations ($EC_{50}$) were calculated for each compound (Table 1).

e) Human Carbonic Anhydrase II Activity

This assay was performed as described in the literature (Armstrong J. et al. Purification and properties of human erythrocyte carbonic anhydrases, J Biol Chem, 1966, 241: 5137-5149). Briefly, in this assay, human carbonic anhydrase II catalyses the conversion of p-nitrophenyl acetate into pnitrophenol. The potential inhibitory effect of test compounds was evaluated by colorimetric determination of prnitrophenol produced during the enzymatic reaction. The optical density levels obtained without inhibitor will be referred to as "total activity". The levels obtained without Inhibitor and without the enzyme will be referred to as "blank" in order to assess any interference with the substrate during the assay (Table 2).

TABLE 1

Inhibition of aromatase, estrone sulfatase and estrogenic potency

| Compounds | Aromatase activity IC$_{50}$ (nM) ± S.E.M. | n | Sulfatase activity IC$_{50}$ (nM) ± S.E.M. | n | Estrogenic potency EC$_{50}$ (nM) ± S.E.M | n |
|---|---|---|---|---|---|---|
| letrozole | 0.47 ± 0.08$^a$ | 8 | nd$^b$ | 6 | nd | 1 |
| anastrozole | 6.93 ± 1.07$^a$ | 6 | nd$^b$ | 6 | nd | 1 |
|  | 2.5 ± 0.6$^c$ | 4 | nd$^c$ | | | |
| A* | nd$^a$ | 3 | 2.5 ± 0.5$^b$ | 4 | nd | 4 |
|  | nd$^c$ | 4 | 3.6 ± 0.8$^c$ | 4 | | |
| Ex 11 | 0.17 ± 0.01$^a$ | 8 | nd$^b$ | 4 | nd | 4 |
| Ex 13 | 0.17 ± 0.03$^a$ | 8 | — | — | nd | 4 |
|  | 0.05 ± 0.02$^c$ | 4 | nd$^c$ | 4 | | |
| Ex 14 | 0.21 ± 0.05$^a$ | 4 | nd$^b$ | 1 | nd | 4 |
| Ex 20 | 0.3$^a$ | 1 | nd$^b$ | 4 | nd | 4 |
| Ex 22 | 0.32 ± 0.40$^a$ | 4 | — | — | nd | 1 |
| Ex 26 | 50.6$^a$ | 1 | nd$^b$ | 1 | — | — |
| Ex 30 | 0.06$^c$ | 1 | — | — | — | — |
| Ex 35 | 2.2 ± 0.7$^c$ | 4 | nd$^c$ | 4 | — | — |
| Ex 36 | 0.61 ± 0.21$^c$ | 4 | nd$^c$ | 4 | — | — |
| Ex 37 | 52.0 ± 9.6$^c$ | 4 | nd$^c$ | 4 | — | — |
| Ex 40 | 0.67 ± 0.10$^a$ | 8 | — | — | nd | 3 |
| Ex 41 | 4.3$^c$ | 1 | — | — | — | — |
| Ex 43 | 0.57 ± 0.16$^a$ | 4 | 5.5 -± 1.1$^b$ | 4 | nd | 4 |
| Ex 45 | 0.13 -± 0.07$^c$ | 4 | 3.4 -± 0.4$^c$ | 4 | nd | 4 |
| Ex 46 | 0.79 ± 0.26$^a$ | 4 | 13.8 ± 2.5$^b$ | 4 | nd | 4 |
| Ex 48 | 0.82 ± 0.12$^a$ | 4 | 2657 ± 257$^b$ | 4 | nd | 1 |
| Ex 51 | 0.34 ± 0.13$^c$ | 4 | 597.2 ± 67.4$^c$ | 4 | — | — |
| Ex 61 | 1.06 ± 0.21$^a$ | 4 | nd$^b$ | 4 | nd | 1 |
| Ex 62 | 81.8$^c$ | 1 | nd$^c$ | 1 | — | — |

A*: sulfamic acid, 3-cycloheptylmethylbenzothiophen-6-yl-1,1-dioxide-ester (described in WO2004/101545)
nd: not detected
Materials & methods:
$^a$aromatase activity alone;
$^b$sulfatase activity alone;
$^c$dual aromatase and sulfatase activity,
$^d$estrogenic potency.

Among the tested compounds, Ex 43, Ex 45 and Ex 46 showed a strong inhibition (Iso about 10 nM) of human estrone sulfatase activity. In addition, the same compounds were shown to be strong inhibitors of aromatase activity (IC$_{50}$<1 nM). Despite this dual activity, They were not estrogenic in vitro.

TABLE 2

Inhibition of human carbonic anhydrase II

| Compounds | Human carbonic anhydrase II activity IC$_{50}$ (nm) ± S.E.M. | n |
|---|---|---|
| acetazolamide | 11.3 ± 1.9 | 4 |
| 6,6,7 COUMATE | 16.1 ± 1.5 | 4 |
| EX 45 | 16.2 ± 3.3 | 4 |
| EX 51 | 6.5 ± 0.9 | 4 |

Ex 45 and Ex 51 inhibited human carbonic anhydrase II in vitro.

Anti Uterotrophic/Anti Steroid Sulfatase Activity In Vivo

Wistar female rats were ovariectomized and left to rest for 4 weeks. Prior to treatment, the absence of cyclicity was checked by vaginal smears. Animals were supplemented with estrone sulfate (EIS) at 50 µg/kg/day s.c., alone or combined with oral administration of potential sulfatase inhibitors, at 1 mg/kg/day for 4 days. The uteri were removed, freed of adjacent tissue and wet weighed (Table 3).

Estrone sulfatase activity is measured according to the method described by Purohit et al., with slight modifications. Briefly, uteri were thawed, weighed and homogenized. Aliquots of the supernatant were treated with dextran-coated charcoal and assayed for sulfatase. E$_1$S activity is assessed after 30 min of incubation with 5 nM of $^3$H-E$_1$S and 20 µM of unlabelled E$_1$S as substrate. Estrone sulfatase activity is expressed as pmol/h/mg protein and reported as percentage of inhibition vs E$_1$S; for uterus weights, results are expressed as % of inhibition of the E$_1$S induced stimulation

TABLE 3

Inhibition of uterus weight

| Compound | % inhibition (uterus weight) | n |
|---|---|---|
| 6,6,7 COUMATE | 81 | 8 |
| Ex 45 | 70 | 8 |

Since there is a direct linear correlation between sulfatase inhibition and uterus weight inhibition (WO 2004/101545), it can be concluded that this uterus activity results from significant inhibition of E$_1$S (>90%). Ex 45 was chosen as a potential inhibitor of estrone sulfatase activity because of its lack of estrogenicity, and significant steroid sulfatase inhibition. These in vivo results were in agreement with in vitro results obtained in JEG-3 cells.

Inhibition of Estradiol Peak, as In Vivo Aromatase Inhibition Model

The aim of this experimentation was to determine a dose-related activity of test compounds in comparison with anastrozole on 17β-estradiol level 24 hours after one oral administration in female rats. Anastrozole, is a potent, non steroidal inhibitor of aromatase, which significantly inhibits estradiol levels at 3 μg/kg, 24 hours after one single oral administration in female rats. One hundred IOPS Wistar female rats, weighing 180 to 200 g, were accommodated by four in stainless steel mesh cages. Animals were allowed free access to a standard diet from Harlan Teklad 2016 pellets. Vaginal smears were performed for each animal, each morning, in order to establish the different phases of cycle. The rats which did not exhibit a regular estrous cycle, were excluded from the experimentation. Starting at 4.00 pm, animals received an oral administration of formulations. 24 hours later, samples of serum were collected and estradiol level were determined as previously described (Table 4).

TABLE 4

Inhibition of estradiol peak

| Compound | % inhibition (estradiol peak) |
|---|---|
| Anastrozole | 56 |
| Ex 45 | 28 |

Ex 45 inhibited estradiol peak in vivo.

Inhibition of Tumor Growth
MCF-7 Xenograft into Nude Mice

MCF7 cells, derived from human breast adenocarcinoma, are injected subcutaneously in ovariectomized athymic nude mice supplemented with a daily administration of subcutaneous estrone sulfate. Xenograft volumes are determined weekly. When tumor volumes reach significant increase, tested compound is orally administered at 1 mg/kg/day for 8 weeks. Xenografts are measured, removed, weighed, and deep frozen for the determination of sulfatase activity, according to methods used for rat uteri ER+ Human Breast Tumor Tissue Xenografted into Nude Rats MCF7 cells (ATCC), derived from human breast adenocarcinoma, were injected subcutaneously in ovariectomized athymic nude mice supplemented with a daily administration of subcutaneous estradiol. Xenograft volumes were determined weekly. After 8 weeks, tumor volumes reached 1000 mm3, providing 500 mg samples of estrogen responsive tissues for each animals. At this time each tumor was sliced and regrafted into naïve ovariectomized nude rat (Rnu/Rnu). Then animals were treated with estrone sulfate as precursor of estradiol by the steroid sulfatase pathway. When tumor volumes reached significant increase, distinct from the placebo, animals were randomized and separated in two groups. The first group was treated with Ex 45 and supplemented with daily administration of estrone sulfate. The second one was sham administered with the vehicle and supplemented with the same dosage of estrone sulfate. Ex 45 was orally administered at 5 mg/kg/day for 5 weeks. Xenografts were measured weekly by electronic Caliper and compared to the estrone sulfate group. (Table 5).

TABLE 5

Inhibition of human breast tumor

| Parameters | | Volume variations (expressed as % of E1S positive control group) | | | |
|---|---|---|---|---|---|
| Treatment | Time | Day 7 | Day 28 | Day 35 | Day 42 |
| E₁S + Ex 45 | | 0 | −26 | −44 | −39 |

When animals were treated with Ex 45, tumor volumes did not increased. On the other hand, simultaneously, groups only treated with estrone sulfate (E1S), tumor volumes were higher. At the end of the experiments, after five weeks of daily treatment, Ex 45 led to a 40%, decrease in tumor volume, showing a clear and well established anticancerous potency.

JEG-3 Xenograft into Nude Mice

The JEG-3 cell line over-expresses both human aromatase and estrone sulfatase enzymes. It is injected subcutaneously into ovariectomized athymic nude mice supplemented with a daily administration of subcutaneous estrone sulfate with or without test compounds (administered at 5 mg/kg/day). In that particular case, and according to their semi-liquid status (choriocarcinoma origin), tumor measures are irrelevant. Nevertheless, an indirect effect of estradiol which is mainly synthesised by the tumour tissue, is obtained on uteri weights. On the other hand, because of the aromatase and sulfatase overexpression in such tumours, enzyme levels are measurable. Enzyme activities are determined according to the above-mentioned methods JEG-3 Xenograft within Nude Rat Supplemented with Estrone Sulfate and Δ4-androstenedione 15 days before JEG-3 cell injection into rats, blood samples are taken to measure basal levels of estradiol plasma. Then, JEG-3 cells are injected subcutaneously in ovariectomized athymic (Rnu/Rnu) nude rat. Animals are supplemented with a daily administration of subcutaneous estrone sulfate and Δ4-androstenedione with or without tested compound (administered at 1 mg/kg/day). After a 21-day period, blood sampling are performed one day after cancerous xenograft and at the end of the experiment. In this experiment estrone sulfate and Δ4-androstenedione are the precursors of estradiol. The effect of estradiol is reflected on the uterus weight after sacrifice. Plasma hormone levels are assayed at the end of the experiments according to the supplier's standard method (DSL, Webster, Tex., USA).

The invention claimed is:

1. An imidazole compound of formula (I):

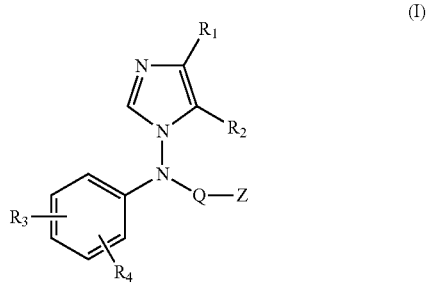

and acid addition salts and stereoisomeric forms thereof, wherein:

$R_1$ and $R_2$ are each independently hydrogen, a $(C_1-C_6)$ alkyl;

Q is selected from the group consisting of C(O), $SO_2$, CONH, $C(O)(CH_2)_n$, $(CH_2)_n(O)$ and $(CH_2)_n$ where n is 0, 1 or 2;

Z is the group:

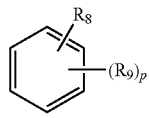

one of $R_3$ and $R_8$ is cyano and the other is $OSO_2NR_{10}R_{11}$;
$R_4$ is hydrogen and $R_9$ is hydrogen, hydroxy, cyano, halogen nitro, $(C_1-C_6)$alkyl, $(C_1-C_6)$alkoxy, trifluoromethyl, acyl, $NR_{10}R_{11}$, $OSO_2NR_{10}R_{11}$, $NR_{12}SO_2NR_{10}R_{11}$, or $CO_2R_{10}$ group;
$R_{10}$, $R_{11}$ and $R_{12}$ are each independently hydrogen or a $(C_1-C_6)$alkyl; and p is 1.

2. A compound according to claim 1, wherein $R_3$ is cyano.

3. A pharmaceutical composition comprising a compound according to claim 1, or a pharmaceutically acceptable acid addition salt thereof, and a pharmaceutically acceptable carrier.

4. An imidazole compound selected from the group consisting of:
Sulfamic acid 4-[N-(4-cyanophenylmethyl)-N-(1H-imidazol-1yl)amino]phenyl ester,
Sulfamic acid 4-{[N-(4-cyanophenyl)-N-(1H-imidazol-1yl)amino]methyl}phenyl ester,
Sulfamic acid 2-chloro-4-{[N-(4-cyanophenyl)-N-(1H-imidazol-1yl)amino]methyl}phenyl ester,
Sulfamic acid 2-bromo-4-{[N-(4-cyanophenyl)-N-(1H-imidazol-1yl)amino]methyl}phenyl ester hydrochloride,
Sulfamic acid 2-methoxy-4-{[N-(4-cyanophenyl)-N-(1H-imidazol-1yl)amino]methyl}phenyl ester,
Sulfamic acid 2,3,5,6-tetrafluoro-4-{[N-(4-cyanophenyl)-N-(1H-imidazol-1yl)amino]methyl}phenyl ester,
4-[N-[(2,2-dioxido-1,2,3-benzoxathiazin-6-yl)methyl]-N-(1H-imidazol-1-yl)amino]benzoitrile,
Sulfamic acid 4-{[N-(4-cyanophenyl)-N-(1H-imidazol-1yl)amino]sulfonyl}phenyl ester hydrochloride,
Sulfamic acid 4-{2-[N-(4-cyanophenyl)-N-(1H-imidazol-1yl)amino]ethoxy}phenyl ester,
Sulfamic acid 4-{[N-(4-cyanophenyl)-N-(1H-imidazol-1yl)-carbamoyl]-methyl}phenyl ester,
Sulfamic acid 4-{[N-(4-cyanophenyl)-N-(1H-imidazol-1yl)amino]-3-oxopropyl}phenyl ester, and
Sulfamic acid 3-(aminosulfonyl)amino-4-{[N-(4-cyanophenyl)-N-(1H-imidazol-1yl)amino]methyl}phenyl ester.

5. The pharmaceutical composition according to claim 3, wherein the compound is as claimed in claim 4.

6. An imidazole compound according to claim 4, which is sulfamic acid 2-bromo-4{[N-(4-cyanophenyl)-N-(1H-imidazol-1yl)amino]-methyl}phenyl ester-, hydrochloride.

* * * * *